United States Patent
Boucher et al.

(10) Patent No.: US 12,228,578 B2
(45) Date of Patent: Feb. 18, 2025

(54) ROCKY MOUNTAIN SPOTTED FEVER DETECTION AND TREATMENT

(71) Applicant: IDEXX LABORATORIES, INC., Westbrook, ME (US)

(72) Inventors: Joshua Michael Boucher, Gray, ME (US); Anton Mestek, Jr., Gorham, ME (US); Clever Madrid, Cumberland, ME (US); Jesse Stephen Buch, Kennebunk, ME (US)

(73) Assignee: IDEXX LABORATORIES, INC., Westbrook, ME (US)

( * ) Notice: Subject to any disclaimer, the term of this patent is extended or adjusted under 35 U.S.C. 154(b) by 157 days.

(21) Appl. No.: 17/554,557

(22) Filed: Dec. 17, 2021

(65) Prior Publication Data

US 2022/0196672 A1    Jun. 23, 2022

Related U.S. Application Data

(60) Provisional application No. 63/126,756, filed on Dec. 17, 2020.

(51) Int. Cl.
*G01N 33/68* (2006.01)
*C07K 14/29* (2006.01)
*G01N 33/569* (2006.01)

(52) U.S. Cl.
CPC ......... *G01N 33/6854* (2013.01); *C07K 14/29* (2013.01); *G01N 33/56911* (2013.01); *C07K 2319/02* (2013.01); *C07K 2319/30* (2013.01); *G01N 2333/29* (2013.01); *G01N 2469/20* (2013.01)

(58) Field of Classification Search
CPC ......... G01N 33/6854; G01N 33/56911; G01N 2333/29; G01N 2469/20; C07K 14/29; C07K 2319/02; C07K 2319/30
See application file for complete search history.

(56) References Cited

U.S. PATENT DOCUMENTS

| | | |
|---|---|---|
| 2004/0022879 A1 | 2/2004 | Larkins |
| 2007/0275962 A1 | 11/2007 | Koul et al. |
| 2007/0280929 A1 | 12/2007 | Hoerr et al. |
| 2008/0194574 A1 | 8/2008 | Eikhoff et al. |
| 2008/0280835 A1 | 11/2008 | Beyreuther et al. |
| 2009/0196912 A1 | 8/2009 | Eickhoff et al. |
| 2009/0275099 A1 | 11/2009 | Glick |
| 2009/0298792 A1 | 12/2009 | Grassauer et al. |
| 2009/0324584 A1 | 12/2009 | Hoerr et al. |
| 2010/0239583 A1 | 9/2010 | Murthy et al. |
| 2011/0091995 A1 | 4/2011 | Krah et al. |
| 2011/0152217 A1 | 6/2011 | Wheeler et al. |
| 2011/0172285 A1 | 7/2011 | Macherla et al. |
| 2011/0184025 A1 | 7/2011 | Hensel |
| 2012/0021004 A1 | 1/2012 | Parker et al. |
| 2013/0018029 A1 | 1/2013 | Yu |
| 2013/0023512 A1 | 1/2013 | Chaudhary et al. |
| 2013/0121915 A1* | 5/2013 | Paas ............ C07K 14/195 424/9.1 |
| 2013/0259955 A1 | 10/2013 | Chen et al. |
| 2014/0256826 A1 | 9/2014 | Lemire et al. |
| 2015/0111873 A1 | 4/2015 | Eickhoff et al. |
| 2015/0274782 A1 | 10/2015 | Cai et al. |
| 2016/0030452 A1 | 2/2016 | Waugh et al. |
| 2016/0333056 A1 | 11/2016 | Lundburg et al. |
| 2016/0339071 A1 | 11/2016 | Tufenkji et al. |
| 2017/0000881 A1 | 1/2017 | Thielemans et al. |
| 2018/0071336 A1 | 3/2018 | Barker et al. |
| 2018/0155301 A1 | 6/2018 | Heckeroth et al. |
| 2018/0296656 A1 | 10/2018 | Crowe et al. |
| 2018/0311202 A1 | 11/2018 | Silver |
| 2020/0164055 A1 | 5/2020 | Ganta |

FOREIGN PATENT DOCUMENTS

WO    2011125015 A2    10/2011

OTHER PUBLICATIONS

Breitschwerdt et al, "Efficacy of Doxycycline, Azithromycin, or Trovafloxacin for Treatment of Experimental Rocky Mountain Spotted Fever in Dogs", Antimicrobial Agents and Chemotherapy, vol. 43, No. 4, pp. 813-821, Jan. 30, 1999.
Levin et al, "Clinical Presentation, Convalescence, and Relapse of Rocky Mountain Spotted Fever in Dogs Experimentally Infected via Tick Bite", PLOS One, 19 pages, Dec. 26, 2014.
Parola et al, "Tick- and flea-borne rickettsial emerging zoonoses", Vet. Res., vol. 36, pp. 469-492, Aug. 5, 2004.
Surface cell antigen Sca2 [*Rickettsia rickettsii* str. Morgan], NCBI Reference Sequence: YP_005285672.1, Feb. 3, 2015, 2 pages.
VUT family protein [Rickettsia rickettsii], Accession: WP_012150928, Jul. 22, 2021, 1page.
Chan et al., "Molecular Basis of Immunity to Rickettsial Infection Conferred through Outer Membrane Protein B", Infection and Immunity, vol. 79, No. 6, Jun. 2011, pp. 2303-2313.
International Search Report of The International Searching Authority issued in International Application No. PCT/US2021/064065, dated Jul. 5, 2022, 5 pages.

(Continued)

*Primary Examiner* — Nelson B Moseley, II
*Assistant Examiner* — Alyssa Rae Stonebraker
(74) *Attorney, Agent, or Firm* — Lisa Hillman; Lathrop GPM LLP

(57) ABSTRACT

Rocky Mountain Spotted Fever (RMSF) is a vector borne disease that is caused by *Rickettsia rickettsii* infection. It is challenging to identify the disease in dogs and other mammals due to the cross-reacting antibodies from non-pathogenic *Rickettsia* spp. Provided herein are compositions and methods for detection and treatment of Rocky Mountain spotted fever ("RMSF"). The compositions specifically detect *Rickettsia rickettsii* and do not cross-react with other *Rickettsia* species providing rapid and accurate detection and diagnosis of RMSF.

23 Claims, 10 Drawing Sheets

Figure 1:
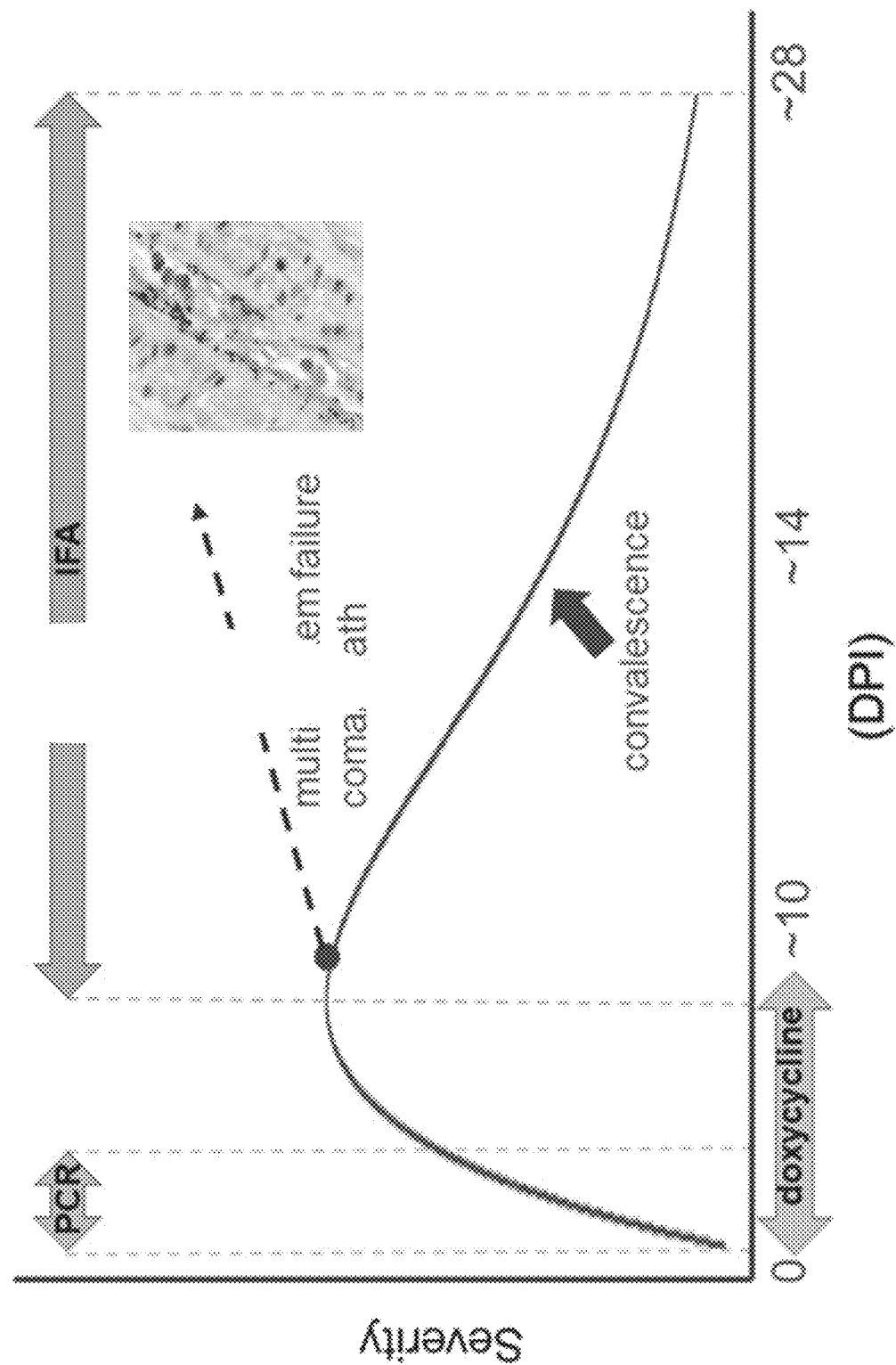
Figure 2:
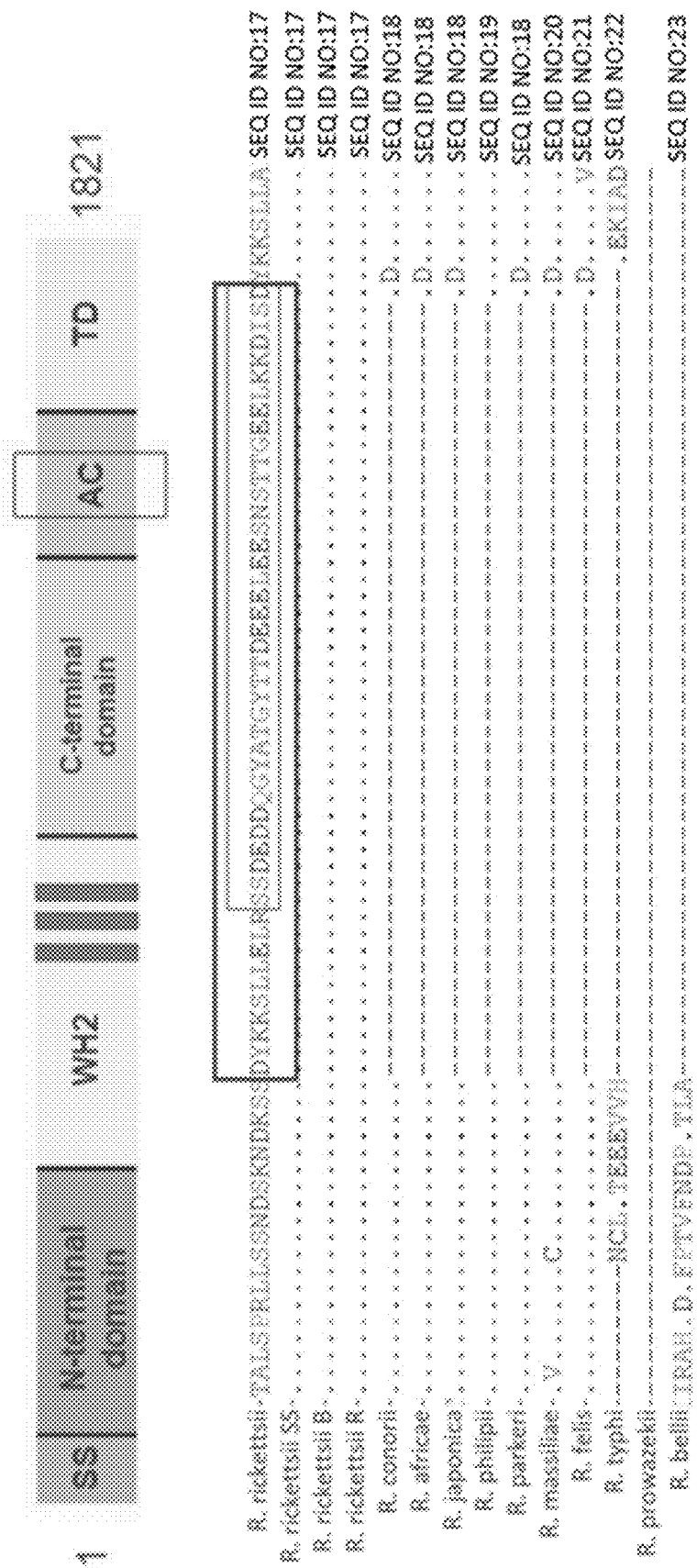

Specification includes a Sequence Listing.

(56) References Cited

OTHER PUBLICATIONS

Written Opinion of The International Searching Authority issued in International Application No. PCT/US2021/064065, dated Jul. 5, 2022, 10 pages.
NIH National Library of Medicine, "surface cell antigen Sca2 [*Rickettsia rickettsii* str. Morgan]", GenBank Accession No. AJG33947.1. Feb. 3, 2015.
NIH National Library of Medicine, "surface cell antigen Sca2 [*Rickettsia rickettsii* str. R]", GenBank Accession No. AJG32613.1, Feb. 3, 2015.
Parola et al., "Tick- and flea-borne rickettsial emerging zoonoses", Veterinary Research, May 2005, 36(3): 469-492.

* cited by examiner

FIG. 3

| | |
|---|---|
| PDX6<br>SEQ ID NO:1 | CDYKKSLLELRSSDEDDQGYATGYTTDEELEESNTTGEELKKDISD |
| PDX7<br>SEQ ID NO:2 | CSSDEDDQGYATGYTTDEELEESNTTGEELKKDISD |
| TDX1779<br>SEQ ID NO:3 | MDWTWRVFLLALATGVHS-PDX6-PDX6-8xHIS-epitope tag |
| TDX1780<br>SEQ ID NO:4 | MDWTWRVFLLALATGVHS-PDX6-PDX6-PDX6-8xHIS-epitope tag |

SEQUENCE LISTING

```
<160> NUMBER OF SEQ ID NOS: 48

<210> SEQ ID NO 1
<211> LENGTH: 48
<212> TYPE: PRT
<213> ORGANISM: Artificial Sequence
<220> FEATURE:
<223> OTHER INFORMATION: PDX6
<220> FEATURE:
<221> NAME/KEY: X
<222> LOCATION: (9)..(9)
<223> OTHER INFORMATION: The X at position 9 can be E or A
<220> FEATURE:
<221> NAME/KEY: X
<222> LOCATION: (34)..(34)
<223> OTHER INFORMATION: The X at position 34 can be G or S

<400> SEQUENCE: 1

Cys Asp Tyr Lys Lys Ser Leu Leu Xaa Leu Arg Ser Ser Asp Glu Asp
1               5                   10                  15

Asp Gln Gly Tyr Ala Thr Gly Tyr Thr Thr Asp Glu Glu Glu Leu Glu
            20                  25                  30

Glu Xaa Asn Ser Thr Thr Gly Glu Glu Leu Lys Lys Asp Ile Ser Asp
        35                  40                  45

<210> SEQ ID NO 2
<211> LENGTH: 38
<212> TYPE: PRT
<213> ORGANISM: Artificial Sequence
<220> FEATURE:
<223> OTHER INFORMATION: PDX7
<220> FEATURE:
<221> NAME/KEY: X
<222> LOCATION: (24)..(24)
<223> OTHER INFORMATION: The X at position 24 can be G or S

<400> SEQUENCE: 2

Cys Ser Ser Asp Glu Asp Asp Gln Gly Tyr Ala Thr Gly Tyr Thr Thr
1               5                   10                  15

Asp Glu Glu Glu Leu Glu Glu Xaa Asn Ser Thr Thr Gly Glu Glu Leu
            20                  25                  30

Lys Lys Asp Ile Ser Asp
        35

<210> SEQ ID NO 3
<211> LENGTH: 172
<212> TYPE: PRT
<213> ORGANISM: Artificial Sequence
<220> FEATURE:
<223> OTHER INFORMATION: TDX1779

<400> SEQUENCE: 3

Met Asp Trp Thr Trp Arg Val Phe Phe Leu Leu Ala Leu Ala Thr Gly
1               5                   10                  15

Val His Ser Cys Asp Tyr Lys Lys Ser Leu Leu Glu Leu Arg Ser Ser
            20                  25                  30

Asp Glu Asp Asp Gln Gly Tyr Ala Thr Gly Tyr Thr Thr Asp Glu Glu
        35                  40                  45

Glu Leu Glu Glu Ser Asn Ser Thr Thr Gly Glu Glu Leu Lys Lys Asp
    50                  55                  60

Ile Ser Asp Asp Tyr Lys Lys Ser Leu Leu Glu Leu Arg Ser Ser Asp
65              70                  75                  80

Glu Asp Asp Gln Gly Tyr Ala Thr Gly Tyr Thr Thr Asp Glu Glu Glu
            85                  90                  95
```

```
Leu Glu Glu Ser Asn Ser Thr Thr Gly Glu Glu Leu Lys Lys Asp Ile
                100                 105                 110

Ser Asp Asp Tyr Lys Lys Ser Leu Leu Glu Leu Arg Ser Ser Asp Glu
            115                 120                 125

Asp Asp Gln Gly Tyr Ala Thr Gly Tyr Thr Thr Asp Glu Glu Glu Leu
        130                 135                 140

Glu Glu Ser Asn Ser Thr Thr Gly Glu Glu Leu Lys Lys Asp Ile Ser
145                 150                 155                 160

Asp Ala Ala Ala His His His His His His His
                165                 170

<210> SEQ ID NO 4
<211> LENGTH: 266
<212> TYPE: PRT
<213> ORGANISM: Artificial Sequence
<220> FEATURE:
<223> OTHER INFORMATION: TDX1780

<400> SEQUENCE: 4

Met Asp Trp Thr Trp Arg Val Phe Phe Leu Leu Ala Leu Ala Thr Gly
1               5                   10                  15

Val His Ser Cys Asp Tyr Lys Lys Ser Leu Leu Glu Leu Arg Ser Ser
                20                  25                  30

Asp Glu Asp Asp Gln Gly Tyr Ala Thr Gly Tyr Thr Thr Asp Glu Glu
            35                  40                  45

Glu Leu Glu Glu Ser Asn Ser Thr Thr Gly Glu Glu Leu Lys Lys Asp
        50                  55                  60

Ile Ser Asp Asp Tyr Lys Lys Ser Leu Leu Glu Leu Arg Ser Ser Asp
65                  70                  75                  80

Glu Asp Asp Gln Gly Tyr Ala Thr Gly Tyr Thr Thr Asp Glu Glu Glu
                85                  90                  95

Leu Glu Glu Ser Asn Ser Thr Thr Gly Glu Glu Leu Lys Lys Asp Ile
                100                 105                 110

Ser Asp Asp Tyr Lys Lys Ser Leu Leu Glu Leu Arg Ser Ser Asp Glu
            115                 120                 125

Asp Asp Gln Gly Tyr Ala Thr Gly Tyr Thr Thr Asp Glu Glu Glu Leu
        130                 135                 140

Glu Glu Ser Asn Ser Thr Thr Gly Glu Glu Leu Lys Lys Asp Ile Ser
145                 150                 155                 160

Asp Asp Tyr Lys Lys Ser Leu Leu Glu Leu Arg Ser Ser Asp Glu Asp
                165                 170                 175

Asp Gln Gly Tyr Ala Thr Gly Tyr Thr Thr Asp Glu Glu Glu Leu Glu
        180                 185                 190

Glu Ser Asn Ser Thr Thr Gly Glu Glu Leu Lys Lys Asp Ile Ser Asp
            195                 200                 205

Asp Tyr Lys Lys Ser Leu Leu Glu Leu Arg Ser Ser Asp Glu Asp Asp
        210                 215                 220

Gln Gly Tyr Ala Thr Gly Tyr Thr Thr Asp Glu Glu Glu Leu Glu Glu
225                 230                 235                 240

Ser Asn Ser Thr Thr Gly Glu Glu Leu Lys Lys Asp Ile Ser Asp Ala
                245                 250                 255

Ala Ala His His His His His His His
            260                 265

<210> SEQ ID NO 5
```

```
<211> LENGTH: 38
<212> TYPE: PRT
<213> ORGANISM: Artificial Sequence
<220> FEATURE:
<223> OTHER INFORMATION: PDX21

<400> SEQUENCE: 5

Met Leu Phe Asp Lys Ile Lys Ser Lys Arg Lys Gly Lys Ser Met Ser
1               5                   10                  15

Asn Ile Asn Ala Lys Phe Tyr Ile Pro Leu Val Ser Leu Leu Gly Val
            20                  25                  30

Phe Ile Tyr Leu Leu Asn
        35

<210> SEQ ID NO 6
<211> LENGTH: 37
<212> TYPE: PRT
<213> ORGANISM: Artificial Sequence
<220> FEATURE:
<223> OTHER INFORMATION: PDX39

<400> SEQUENCE: 6

Cys Lys Glu Val Leu Tyr Lys Ser Ala Tyr Ser Leu Thr Val Tyr Ile
1               5                   10                  15

Ser Ile Phe Leu Val Gln Lys Val Tyr Gly Asn Asn Gly Ser Val Arg
            20                  25                  30

Ala Leu Lys Asn Phe
        35

<210> SEQ ID NO 7
<211> LENGTH: 38
<212> TYPE: PRT
<213> ORGANISM: Artificial Sequence
<220> FEATURE:
<223> OTHER INFORMATION: PDX40

<400> SEQUENCE: 7

Cys Leu Phe Asp Lys Ile Lys Ser Lys Arg Lys Gly Lys Ser Met Ser
1               5                   10                  15

Asn Ile Asn Ala Lys Phe Tyr Ile Pro Leu Val Ser Leu Leu Gly Val
            20                  25                  30

Phe Ile Tyr Leu Leu Asn
        35

<210> SEQ ID NO 8
<211> LENGTH: 200
<212> TYPE: PRT
<213> ORGANISM: Artificial Sequence
<220> FEATURE:
<223> OTHER INFORMATION: The Rickettsia vitamin uptake transporter VUT
      family protein

<400> SEQUENCE: 8

Met Leu Phe Asp Lys Ile Lys Ser Lys Arg Lys Gly Lys Cys Met Ser
1               5                   10                  15

Asn Ile Asn Ala Lys Phe Tyr Ile Pro Leu Val Ser Leu Leu Gly Val
            20                  25                  30

Phe Ile Tyr Leu Leu Asn Cys Phe Asn Lys Ile Ser Gln Cys Ser Leu
        35                  40                  45

Val Phe Val Phe Leu Ala Ile Thr Thr Asn Ile Ile Ser Glu Leu Tyr
    50                  55                  60

Gly Arg Lys Arg Ala Leu Ile Ala Val Ala Leu Cys Ile Ile Val Ser
```

```
                65                  70                  75                  80
        Phe Gly Leu Leu Trp Asn Phe Asn Tyr Tyr Ile His Gly Arg Val Ile
                        85                  90                  95

Lys Gly Val Val Phe Ala Ser Phe Val Ser Val Leu Ser Thr Tyr
                    100                 105                 110

Cys Ser Thr Ser Ile Phe Ser Gln Leu Lys Pro Arg Cys Ser Leu Asn
                    115                 120                 125

Thr Arg Asn Phe Ala Ser Leu Ile Met Cys Ala Val Val Asp Gly Ile
                130                 135                 140

Val Met Ser Gly Phe Phe Val Asn Val Phe Ser Thr Ser Lys Val Leu
        145                 150                 155                 160

Ser Ile Phe Tyr Lys Glu Val Leu Tyr Lys Cys Ala Tyr Ser Leu Thr
                        165                 170                 175

Val Tyr Ile Cys Ile Phe Leu Val Gln Lys Val Tyr Gly Asn Asn Gly
                    180                 185                 190

Ser Val Arg Ala Leu Lys Asn Phe
                    195                 200
```

<210> SEQ ID NO 9
<211> LENGTH: 10
<212> TYPE: PRT
<213> ORGANISM: Artificial Sequence
<220> FEATURE:
<223> OTHER INFORMATION: HA epitope tag

<400> SEQUENCE: 9

```
Tyr Pro Tyr Asp Val Pro Asp Tyr Ala Cys
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: myc epitope tag

<400> SEQUENCE: 10

```
Glu Gln Lys Leu Ile Ser Glu Glu Asp Leu Cys
1               5                   10
```

<210> SEQ ID NO 11
<211> LENGTH: 14
<212> TYPE: PRT
<213> ORGANISM: Artificial Sequence
<220> FEATURE:
<223> OTHER INFORMATION: V5 epitope tag

<400> SEQUENCE: 11

```
Gly Lys Pro Ile Pro Asn Pro Leu Leu Gly Leu Asp Ser Thr
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: E-tag epitope tag

<400> SEQUENCE: 12

```
Gly Ala Pro Val Pro Tyr Pro Asp Pro Leu Glu Pro Arg
1               5                   10
```

```
<210> SEQ ID NO 13
<211> LENGTH: 11
<212> TYPE: PRT
<213> ORGANISM: Artificial Sequence
<220> FEATURE:
<223> OTHER INFORMATION: VSV-g epitope tag

<400> SEQUENCE: 13

Tyr Thr Asp Ile Glu Met Asn Arg Leu Gly Lys
1               5                   10

<210> SEQ ID NO 14
<211> LENGTH: 7
<212> TYPE: PRT
<213> ORGANISM: Artificial Sequence
<220> FEATURE:
<223> OTHER INFORMATION: 6xHis epitope tag

<400> SEQUENCE: 14

His His His His His His His
1               5

<210> SEQ ID NO 15
<211> LENGTH: 12
<212> TYPE: PRT
<213> ORGANISM: Artificial Sequence
<220> FEATURE:
<223> OTHER INFORMATION: HSV epitope tag

<400> SEQUENCE: 15

Gln Pro Glu Leu Ala Pro Glu Asp Pro Glu Asp Cys
1               5                   10

<210> SEQ ID NO 16
<211> LENGTH: 8
<212> TYPE: PRT
<213> ORGANISM: Artificial Sequence
<220> FEATURE:
<223> OTHER INFORMATION: FLAG epitope tag

<400> SEQUENCE: 16

Asp Tyr Lys Asp Asp Asp Asp Lys
1               5

<210> SEQ ID NO 17
<211> LENGTH: 73
<212> TYPE: PRT
<213> ORGANISM: Artificial Sequence
<220> FEATURE:
<223> OTHER INFORMATION: SCA2 auto chaperone region from Rickettsia
      rickettsii species

<400> SEQUENCE: 17

Thr Ala Leu Ser Pro Arg Leu Leu Ser Ser Asn Asp Ser Lys Asn Asp
1               5                   10                  15

Lys Ser Ser Asp Tyr Lys Lys Ser Leu Leu Glu Leu Arg Ser Ser Asp
            20                  25                  30

Glu Asp Asp Gln Gly Tyr Ala Thr Gly Tyr Thr Thr Asp Glu Glu Glu
        35                  40                  45

Leu Glu Glu Ser Asn Ser Thr Thr Gly Glu Glu Leu Lys Lys Asp Ile
    50                  55                  60

Ser Asp Tyr Lys Lys Ser Leu Leu Ala
65                  70

<210> SEQ ID NO 18
```

```
<211> LENGTH: 27
<212> TYPE: PRT
<213> ORGANISM: Artificial Sequence
<220> FEATURE:
<223> OTHER INFORMATION: SCA2 auto chaperone region from Rickettsia
      conorii, Rickettsia africae, Rickettsia japonica, and Rickettsia
      parkeri species

<400> SEQUENCE: 18

Thr Ala Leu Ser Pro Arg Leu Leu Ser Ser Asn Asp Ser Lys Asn Asp
1               5                   10                  15

Lys Ser Ser Asp Asp Lys Lys Ser Leu Leu Ala
            20                  25

<210> SEQ ID NO 19
<211> LENGTH: 27
<212> TYPE: PRT
<213> ORGANISM: Artificial Sequence
<220> FEATURE:
<223> OTHER INFORMATION: SCA2 auto chaperone region from Rickettsia
      philipii species

<400> SEQUENCE: 19

Thr Ala Leu Ser Pro Arg Leu Leu Ser Ser Asn Asp Ser Lys Asn Asp
1               5                   10                  15

Lys Ser Ser Asp Tyr Lys Lys Ser Leu Leu Ala
            20                  25

<210> SEQ ID NO 20
<211> LENGTH: 27
<212> TYPE: PRT
<213> ORGANISM: Artificial Sequence
<220> FEATURE:
<223> OTHER INFORMATION: SCA2 auto chaperone region from Rickettsia
      massiliae species

<400> SEQUENCE: 20

Thr Val Leu Ser Pro Arg Leu Leu Cys Ser Asn Asp Ser Lys Asn Asp
1               5                   10                  15

Lys Ser Ser Asp Asp Lys Lys Ser Leu Leu Ala
            20                  25

<210> SEQ ID NO 21
<211> LENGTH: 27
<212> TYPE: PRT
<213> ORGANISM: Artificial Sequence
<220> FEATURE:
<223> OTHER INFORMATION: SCA2 auto chaperone region from Rickettsia
      felis species

<400> SEQUENCE: 21

Thr Ala Leu Ser Pro Arg Leu Leu Ser Ser Asn Asp Ser Lys Asn Asp
1               5                   10                  15

Lys Ser Ser Asp Asp Lys Lys Ser Leu Leu Val
            20                  25

<210> SEQ ID NO 22
<211> LENGTH: 17
<212> TYPE: PRT
<213> ORGANISM: Artificial Sequence
<220> FEATURE:
<223> OTHER INFORMATION: SCA2 auto chaperone region from Rickettsia
      typhi species

<400> SEQUENCE: 22

Asn Cys Leu Asp Thr Glu Glu Glu Val Val His Lys Glu Lys Ile Ala
```

```
1               5                   10                  15

Asp

<210> SEQ ID NO 23
<211> LENGTH: 19
<212> TYPE: PRT
<213> ORGANISM: Artificial Sequence
<220> FEATURE:
<223> OTHER INFORMATION: SCA2 auto chaperone region from Rickettsia
      bellii species

<400> SEQUENCE: 23

Ile Arg Ala His Pro Asp Leu Phe Pro Thr Val Phe Asn Asp Pro Asp
1               5                   10                  15

Thr Leu Ala

<210> SEQ ID NO 24
<211> LENGTH: 19
<212> TYPE: PRT
<213> ORGANISM: Artificial Sequence
<220> FEATURE:
<223> OTHER INFORMATION: secretory signal sequence

<400> SEQUENCE: 24

Met Asp Trp Thr Trp Arg Val Phe Phe Leu Leu Ala Leu Ala Thr Gly
1               5                   10                  15

Val His Ser

<210> SEQ ID NO 25
<211> LENGTH: 19
<212> TYPE: PRT
<213> ORGANISM: Artificial Sequence
<220> FEATURE:
<223> OTHER INFORMATION: secretory signal sequence

<400> SEQUENCE: 25

Met Asp Trp Thr Trp Arg Ile Leu Phe Leu Val Ala Ala Ala Thr Gly
1               5                   10                  15

Thr His Ala

<210> SEQ ID NO 26
<211> LENGTH: 22
<212> TYPE: PRT
<213> ORGANISM: Artificial Sequence
<220> FEATURE:
<223> OTHER INFORMATION: secretory signal sequence

<400> SEQUENCE: 26

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 27
<211> LENGTH: 25
<212> TYPE: PRT
<213> ORGANISM: Artificial Sequence
<220> FEATURE:
<223> OTHER INFORMATION: secretory signal sequence

<400> SEQUENCE: 27

Met Ala Thr Gly Ser Arg Thr Ser Leu Leu Leu Ala Phe Gly Leu Leu
1               5                   10                  15
```

Cys Leu Trp Leu Gln Glu Gly Ser Ala
            20                  25

<210> SEQ ID NO 28
<211> LENGTH: 16
<212> TYPE: PRT
<213> ORGANISM: Artificial Sequence
<220> FEATURE:
<223> OTHER INFORMATION: secretory signal sequence

<400> SEQUENCE: 28

Met Pro Leu Leu Leu Leu Leu Pro Leu Leu Trp Ala Gly Ala Leu Ala
1               5                   10                  15

<210> SEQ ID NO 29
<211> LENGTH: 35
<212> TYPE: PRT
<213> ORGANISM: Artificial Sequence
<220> FEATURE:
<223> OTHER INFORMATION: secretory signal sequence

<400> SEQUENCE: 29

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg
        35

<210> SEQ ID NO 30
<211> LENGTH: 21
<212> TYPE: PRT
<213> ORGANISM: Artificial Sequence
<220> FEATURE:
<223> OTHER INFORMATION: secretory signal sequence

<400> SEQUENCE: 30

Met Lys Gln Ser Thr Ile Ala Leu Ala Leu Leu Pro Leu Leu Phe Thr
1               5                   10                  15

Pro Val Lys Thr Ala
            20

<210> SEQ ID NO 31
<211> LENGTH: 21
<212> TYPE: PRT
<213> ORGANISM: Artificial Sequence
<220> FEATURE:
<223> OTHER INFORMATION: secretory signal sequence

<400> SEQUENCE: 31

Met Lys Lys Thr Ala Ile Ala Ile Ala Val Ala Leu Ala Gly Phe Ala
1               5                   10                  15

Thr Val Ala Gln Ala
            20

<210> SEQ ID NO 32
<211> LENGTH: 19
<212> TYPE: PRT
<213> ORGANISM: Artificial Sequence
<220> FEATURE:
<223> OTHER INFORMATION: secretory signal sequence

<400> SEQUENCE: 32

Met Lys Lys Ile Trp Leu Ala Leu Ala Gly Leu Val Leu Ala Phe Ser
1               5                   10                  15

Ala Ser Ala

<210> SEQ ID NO 33
<211> LENGTH: 17
<212> TYPE: PRT
<213> ORGANISM: Artificial Sequence
<220> FEATURE:
<223> OTHER INFORMATION: secretory signal sequence

<400> SEQUENCE: 33

Met Arg Val Leu Leu Phe Leu Leu Ser Leu Phe Met Leu Pro Ala Phe
1               5                   10                  15

Ser

<210> SEQ ID NO 34
<211> LENGTH: 27
<212> TYPE: PRT
<213> ORGANISM: Artificial Sequence
<220> FEATURE:
<223> OTHER INFORMATION: secretory signal sequence

<400> SEQUENCE: 34

Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
            20                  25

<210> SEQ ID NO 35
<211> LENGTH: 39
<212> TYPE: PRT
<213> ORGANISM: Artificial Sequence
<220> FEATURE:
<223> OTHER INFORMATION: secretory signal sequence

<400> SEQUENCE: 35

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
        35

<210> SEQ ID NO 36
<211> LENGTH: 30
<212> TYPE: PRT
<213> ORGANISM: Artificial Sequence
<220> FEATURE:
<223> OTHER INFORMATION: secretory signal sequence

<400> SEQUENCE: 36

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala
            20                  25                  30

<210> SEQ ID NO 37
<211> LENGTH: 25
<212> TYPE: PRT
<213> ORGANISM: Artificial Sequence
<220> FEATURE:
<223> OTHER INFORMATION: secretory signal sequence

<400> SEQUENCE: 37

Met Met Pro Ser Ser Val Ser Trp Gly Ile Leu Leu Ala Gly Leu
1               5                   10                  15

Cys Cys Leu Val Pro Val Ser Leu Ala
            20                  25

<210> SEQ ID NO 38
<211> LENGTH: 46
<212> TYPE: PRT
<213> ORGANISM: Artificial Sequence
<220> FEATURE:
<223> OTHER INFORMATION: secretory signal sequence

<400> SEQUENCE: 38

Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg
        35                  40                  45

<210> SEQ ID NO 39
<211> LENGTH: 21
<212> TYPE: PRT
<213> ORGANISM: Artificial Sequence
<220> FEATURE:
<223> OTHER INFORMATION: secretory signal sequence

<400> SEQUENCE: 39

Met Lys Gly Ser Leu Leu Leu Leu Leu Val Ser Asn Leu Leu Leu Cys
1               5                   10                  15

Gln Ser Val Ala Pro
            20

<210> SEQ ID NO 40
<211> LENGTH: 24
<212> TYPE: PRT
<213> ORGANISM: Artificial Sequence
<220> FEATURE:
<223> OTHER INFORMATION: secretory signal sequence

<400> SEQUENCE: 40

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 41
<211> LENGTH: 99
<212> TYPE: PRT
<213> ORGANISM: Artificial Sequence
<220> FEATURE:
<223> OTHER INFORMATION: secretory signal sequence

<400> SEQUENCE: 41

Met Val Ser Leu Lys Ile Lys Lys Leu Leu Val Ser Leu Leu Leu Asn
1               5                   10                  15

Ala Ile Glu Ala Tyr Ser Asn Asp Thr Ile Tyr Ser Thr Ser Tyr Asn
                20                  25                  30

Asn Gly Ile Glu Ser Thr Pro Ser Tyr Ser Thr Ser Ala Ile Ser Ser
        35                  40                  45

Thr Gly Ser Ser Asn Lys Glu Asn Ala Ile Thr Ser Ser Ser Glu Thr
    50                  55                  60

```
Thr Thr Met Ala Gly Asp Tyr Gly Glu Ser Gly Ser Thr Thr Ile Met
 65                  70                  75                  80

Asp Glu Gln Glu Thr Gly Thr Ser Ser Gln Tyr Ile Ser Val Thr Thr
                 85                  90                  95

Thr Thr Gln

<210> SEQ ID NO 42
<211> LENGTH: 43
<212> TYPE: PRT
<213> ORGANISM: Artificial Sequence
<220> FEATURE:
<223> OTHER INFORMATION: secretory signal sequence

<400> SEQUENCE: 42

Asn Gly Gly Asn Met Ala Ile Lys Lys Ala Ser Leu Ile Ala Leu Leu
 1               5                  10                  15

Pro Leu Phe Thr Ala Ala Ala Ala Ala Thr Asp Ala Glu Thr Ser
                 20                  25                  30

Asn Glu Ser Gly Ser Ser Ser His Leu Lys Ser
             35                  40

<210> SEQ ID NO 43
<211> LENGTH: 84
<212> TYPE: PRT
<213> ORGANISM: Artificial Sequence
<220> FEATURE:
<223> OTHER INFORMATION: secretory signal sequence

<400> SEQUENCE: 43

Met Lys Phe Thr Ser Val Leu Ala Phe Phe Leu Ala Thr Leu Thr Ala
 1               5                  10                  15

Ser Ala Thr Phe Leu Tyr Lys Arg Gln Asn Val Thr Ser Gly Gly Gly
                 20                  25                  30

Thr Val Pro Ile Ile Thr Gly Gly Pro Ala Val Ser Gly Ser Gln Ser
             35                  40                  45

Asn Val Thr Thr Thr Thr Leu Phe Asn Ser Thr Ser Thr Leu Asn Ile
 50                  55                  60

Thr Gln Leu Tyr Gln Ile Ala Thr Asp Val Asn Asp Thr Leu Gln Ser
 65                  70                  75                  80

Glu Ser Ser Ser

<210> SEQ ID NO 44
<211> LENGTH: 100
<212> TYPE: PRT
<213> ORGANISM: Artificial Sequence
<220> FEATURE:
<223> OTHER INFORMATION: secretory signal sequence

<400> SEQUENCE: 44

Met Gln Phe Pro Phe Ala Cys Leu Leu Ser Thr Leu Val Ile Ser Gly
 1               5                  10                  15

Ser Leu Ala Arg Ala Ser Pro Phe Asp Phe Ile Phe Gly Asn Gly Thr
                 20                  25                  30

Gln Gln Ala Gln Ser Gln Ser Glu Ser Gln Gly Gln Val Ser Phe Thr
             35                  40                  45

Asn Glu Ala Ser Gln Asp Ser Ser Thr Thr Leu Val Thr Ala Tyr
 50                  55                  60

Ser Gln Gly Val His Ser His Gln Ser Ala Thr Ile Val Ser Ala Thr
 65                  70                  75                  80
```

-continued

```
Ile Ser Ser Leu Pro Ser Thr Trp Tyr Asp Ala Ser Thr Ser Gln
                85                  90                  95

Thr Ser Val Ser
            100

<210> SEQ ID NO 45
<211> LENGTH: 96
<212> TYPE: PRT
<213> ORGANISM: Artificial Sequence
<220> FEATURE:
<223> OTHER INFORMATION: secretory signal sequence

<400> SEQUENCE: 45

Met Gln Phe Lys Asn Ala Leu Thr Ala Thr Ala Ile Leu Ser Ala Ser
1               5                   10                  15

Ala Leu Ala Ala Asn Ser Thr Thr Ser Ile Pro Ser Ser Cys Ser Ile
                20                  25                  30

Gly Thr Ser Ala Thr Ala Thr Ala Gln Ala Asp Leu Asp Lys Ile Ser
            35                  40                  45

Gln Cys Ser Thr Ile Val Gly Asn Leu Thr Ile Thr Gly Asp Leu Gly
        50                  55                  60

Ser Ala Ala Leu Ala Ser Ile Gln Glu Ile Asp Gly Ser Leu Thr Ile
65                  70                  75                  80

Phe Asn Ser Ser Ser Leu Ser Ser Phe Ser Ala Asp Ile Lys Lys Ile
                85                  90                  95

<210> SEQ ID NO 46
<211> LENGTH: 77
<212> TYPE: PRT
<213> ORGANISM: Artificial Sequence
<220> FEATURE:
<223> OTHER INFORMATION: secretory signal sequence

<400> SEQUENCE: 46

Met Lys Phe Ser Thr Leu Ser Thr Val Ala Ala Ile Ala Ala Phe Ala
1               5                   10                  15

Ser Ala Asp Ser Thr Ser Asp Gly Val Thr Tyr Val Asp Val Thr Thr
                20                  25                  30

Thr Pro Gln Ser Thr Thr Ser Met Val Ser Thr Val Lys Thr Thr Ser
            35                  40                  45

Thr Pro Tyr Thr Thr Ser Thr Ile Ala Thr Leu Ser Thr Lys Ser Ile
        50                  55                  60

Ser Ser Gln Ala Asn Thr Thr Thr His Glu Ile Ser Thr
65                  70                  75

<210> SEQ ID NO 47
<211> LENGTH: 100
<212> TYPE: PRT
<213> ORGANISM: Artificial Sequence
<220> FEATURE:
<223> OTHER INFORMATION: secretory signal sequence

<400> SEQUENCE: 47

Met Phe Val His Arg Leu Trp Thr Leu Ala Phe Pro Phe Leu Val Glu
1               5                   10                  15

Ile Ser Lys Ala Ser Gln Leu Glu Asn Ile Lys Ser Leu Leu Asp Ile
                20                  25                  30

Glu Asp Asn Val Leu Pro Asn Leu Asn Ile Ser Gln Asn Asn Ser Asn
            35                  40                  45

Ala Val Gln Ile Leu Gly Gly Val Asp Ala Leu Ser Phe Tyr Glu Tyr
```

```
                    50                  55                  60
Thr Gly Gln Gln Asn Phe Thr Lys Glu Ile Gly Pro Glu Thr Ser Ser
 65                  70                  75                  80

His Gly Leu Val Tyr Tyr Ser Asn Asn Thr Tyr Ile Gln Leu Glu Asp
                 85                  90                  95

Ala Ser Asp Asp
            100

<210> SEQ ID NO 48
<211> LENGTH: 66
<212> TYPE: PRT
<213> ORGANISM: Artificial Sequence
<220> FEATURE:
<223> OTHER INFORMATION: secretory signal sequence

<400> SEQUENCE: 48

Met Lys Leu Gln Ser Leu Leu Val Ser Ala Ala Val Leu Thr Ser Leu
 1               5                  10                  15

Thr Glu Asn Val Asn Ala Met Ser Pro Asn Asn Ser Tyr Val Pro Ala
                20                  25                  30

Asn Val Thr Cys Asp Asp Asp Ile Asn Leu Val Arg Glu Ala Ser Gly
             35                  40                  45

Leu Ser Asp Asn Glu Tyr Glu Met Leu Lys Lys Arg Asp Ala Tyr Thr
 50                  55                  60

Lys Glu
 65
```

ROCKY MOUNTAIN SPOTTED FEVER DETECTION AND TREATMENT

PRIORITY

This application claims the benefit of U.S. Ser. No. 63/126,756, filed on Dec. 17, 2020, which is incorporated by reference in its entirety.

SEQUENCE LISTING

The instant application contains a Sequence Listing which has been submitted in ASCII format via EFS-Web and is hereby incorporated by reference in its entirety. Said ASCII copy, created on Dec. 16, 2021, is named "331721-000065_sequence_listing_ST25_1.txt" and is about 29 bytes in size.

BACKGROUND

Rocky Mountain Spotted Fever (RMSF) is a vector borne disease that is caused by *Rickettsia rickettsii* infection. It is challenging to identify the disease in dogs due to the cross-reacting antibodies from non-pathogenic *Rickettsia* spp. Therefore, identification of *R. rickettsii* specific genes/proteins is critical for the development of an effective diagnostic test. RMSF is a zoonotic disease that is transmitted to dogs mostly by American dog tick (*Dermacentor variabilis*), Rocky Mountain wood tick (*Dermacentor andersonii*) and other ticks such as *Ambylomma* and *Rhipicephalus*. Ticks infected with *R. rickettsii* bite humans, dogs, deer, and other animals thereby spreading the infectious bacteria. *R. rickettsii* enter the bloodstream during tick bite and invade the vascular cells of the microcirculatory system, often resulting in widespread vascular damage.

*R. rickettsii* is phylogenetically closely related to other *Rickettsia* spp and endosymbionts. Although the genomes of several different species of *Rickettsia* have been sequenced, the challenge for the identification of diagnostic antigen is the cross-reacting antibodies from both non-pathogenic or endosymbionts and other *Rickettsia* spp. The current diagnosis of RMSF is performed by PCR, IFA, and culture. However, these diagnostic methods have certain limitations in detecting the infection (Parola et al., (2005) *Veterinary research*, 36(3), 469-492; Breitschwerdt et al., (1999) *Antimicrobial agents and chemotherapy*, 43(4), 813-821; Levin et al. (2014) *PloS one*, 9(12).

RMSF is one of the most lethal tick-borne diseases. Infection of humans with *R. rickettsii* can result in a ~15% mortality rate if untreated. Human cases have been steadily on the rise over the last decade. The prevalence in canines can vary from as low as 0.1% in non-endemic areas to as high as 14% or greater in endemic areas or during a local outbreak. Novel markers are needed for *R. rickettsii* infection that will lead to early (days 4-14 DPI infection or earlier) and highly specific detection of anti-*Rickettsia rickettsii* antibodies. Furthermore, there is a need for a species-specific diagnostic test for *R. rickettsii*.

SUMMARY

An embodiment provides a polypeptide comprising (i) 90% or more sequence identity to a polypeptide as set forth in SEQ ID NO:1, 2, 3, 4, 5, 6, or 7; (ii) a fusion protein made up of two, three, four, five, six, seven or more polypeptides having 90% or more sequence identity to SEQ ID NO:1, 2, 3, 4, 5, 6, or 7; or (iii) a fusion protein made up of at least two polypeptides having 90% or more sequence identity to SEQ ID NO:1, 2, 3, 4, 5, 6, or 7.

Another embodiment provides a polypeptide having less than 75 total amino acids and comprising 90% or more sequence identity to a polypeptide as set forth in SEQ ID NO:1, 2, 5, 6, or 7.

Yet another embodiment provides a polypeptide having less than 350 total amino acids and comprising 90% or more sequence identity to a polypeptide as set forth in SEQ ID NO:3 or 4.

In an embodiment the polypeptides are not naturally occurring. The polypeptides can be lyophilized, desiccated, or dried. The polypeptides can further comprise one or more labels or tags. The polypeptides can be immobilized to a support. The polypeptides can be present in an immunocomplex with one or more antibodies that specifically bind to a polypeptide as set forth in SEQ ID NO:1, 2, 3, 4, 5, 6, or 7.

Still another embodiment provides a method of detecting anti-*Rickettsia rickettsii* antibodies or specific binding fragments thereof. The method can comprise contacting a test sample with one or more polypeptides comprising 90% or more sequence identity to a polypeptide as set forth in SEQ ID NO:1, 2, 3, 4, 5, 6, or 7; and detecting complexes of anti-*Rickettsia rickettsii* antibodies or specific binding fragments thereof and the one or more polypeptides. The one or more polypeptides can be immobilized to a support. The complexes can be detected using one or more secondary antibodies or specific binding fragments thereof that specifically bind anti-*Rickettsia rickettsii* antibodies or specific binding fragments thereof. The secondary antibodies or specific binding fragments thereof can comprise one or more tags or labels. The complexes can be detected using one or more detector polypeptides comprising 90% or more sequence identity to a polypeptide as set forth in SEQ ID NO:1, 2, 3, 4, 5, 6, or 7. The one or more detector polypeptides can comprise a label or tag. The polypeptide can comprise 90% or more sequence identity to a polypeptide as set forth in SEQ ID NO:1, 2, 5, 6, or 7 and further can include one or more secretory signal sequences, one or more epitope tags, or one or more secretory signal sequences and one or more epitope tags.

Another embodiment provides a method for diagnosing a disease caused by *Rickettsia rickettsii* in a subject. The method can comprise contacting a test sample with one or more polypeptides comprising 90% or more sequence identity to a polypeptide as set forth in SEQ ID NO:1, 2, 3, 4, 5, 6, or 7; and detecting complexes of anti-*Rickettsia rickettsii* antibodies or specific binding fragments thereof and the one or more polypeptides. The subject can be infected with *Rickettsia rickettsii* for less than about 4, 5, 6, 7, 8, or 9 days. The method can further comprise comparing an amount of the complexes in the sample to a control sample or control standard, wherein elevated levels of the complexes as compared to the control sample or control standard is an indication of a disease caused by *Rickettsia rickettsii*. The method can further comprise administering a treatment for a disease caused by *Rickettsia rickettsii* where the complexes are detected. The method can further comprise determining an amount of the anti-*Rickettsia rickettsii* antibodies or specific binding fragments thereof in the sample. The subject can be a human or a non-human animal. The test sample can be whole blood, plasma, serum, lymph fluid, urine, feces, nasal swab, throat swab, saliva, an environmental sample, or any other suitable sample.

In an embodiment, the anti-*Rickettsia rickettsii* antibodies or specific binding fragments thereof can be detected by a competitive immunoassay, a sandwich immunoassay, an enzyme-linked immunosorbent assay (ELISA), an immunohistochemical assay, a turbidimetric immunoassay, a particle-enhanced turbidimetric immunoassay, a radioimmunoassay (RIA), a fluorescent immunosorbent assay (FIA), a multiplex immunoassay, a protein/peptide array immunoassay, a solid phase radioimmunoassay (SPRIA), an indirect immunofluorescence assay (IIF), a chemiluminescent immunoassay (CIA), a particle based multianalyte test (PMAT), a dot blot assay, a western blot assay, surface plasmon resonance (SPR), isothermal titration calorimetry (ITC), microscale thermophoresis (MST), biolayer interferometry, or grating-coupled interferometry.

Yet another embodiment provides a kit for diagnosing a disease caused by *Rickettsia rickettsii*. A kit can comprise one or more polypeptides comprising 90% or more sequence identity to a polypeptide as set forth in SEQ ID NO:1, 2, 3, 4, 5, 6, or 7, wherein the polypeptide is not naturally occurring; and one or more reagents that facilitate binding of the one or more polypeptides to anti-*Rickettsia rickettsii* antibodies or specific binding fragments thereof present in a test sample.

BRIEF DESCRIPTION OF THE DRAWINGS

FIG. 1 shows a hypothetical time course for RMSF infection and available diagnostics at selected times post infection. Severity, mortality risk, and seroconversion are dependent on the dose of pathogen, immune response of the infected and strain of *Rickettsia*. The x-axis represents days post infection (DPI) and the y-axis represents severity of infection. The curve is a representative time-course of RMSF infection. As infection progresses over time, the afflicted will either seroconvert and eliminate the infection or succumb to multi-system failure and potentially death. The insert shows a longitudinal section of *R. rickettsii* infected vasculature. The arrow with doxycycline represents the time window for effective treatment. *R. rickettsii* are evolutionarily primed to rapidly exit the blood stream and replicate in the vascular endothelial cells (see insert), thus rendering PCR from a blood draw ineffective beyond the first few days of infection. IFA which detects seroconversion lacks specificity and is generally very laborious, rendering it ineffective for rapid or in-clinic guidance on treatment.

FIG. 2 shows a schematic of the extracellular protein SCA2 in the top pane. In the autochaperone domain (AC) of the extracellular protein SCA2, boxed, resides a stretch of amino acids that is only present in *R. rickettsii* strains. The bottom pane shows sequences for the SCA2 auto chaperone region from *Rickettsia* species. The entire unique region (larger horizontal box) is PDX6, while a slightly truncated region (smaller horizontal box) is PDX7.

FIG. 3 shows specific reagents generated around the *R. rickettsii*-specific region of Sca2 protein. PDX6 is representative of the whole unique region of interest, while PDX7 is a slightly truncated sequence. Two recombinant fusion proteins were made consisting of 3 repeats of the PDX6 region (TDX1779) or 5 repeats of the PDX6 region (TDX1780). Recombinant proteins were also synthesized with 8× His tags and epitope tags.

FIG. 4 shows a schematic of the PDX7 polypeptide conjugated to amino beads with a primary and secondary antibody. Detection of antibody binding was reported using biotinylated rabbit anti canine IgG.

FIG. 5 shows PDX7 reactivity to experimental (pooled) sera on multiplex. PDX7 fluorescence intensity (MFI) of PDX7 before infection and 4, 7, 11, 14, 21, 25, 32, and 39 days post infection (PDI). PDX7 was conjugated to amino beads and incubated against pooled serum from *R. rickettsii* experimentally infected canines. Detection of the antibody binding was reported using biotinylated rabbit anti-canine IgG. The Ideal treatment window lies in the range between PID4 and PID21.

FIG. 6 shows TDX1779 and 1780 reactivity to experimental sera on multiplex (Indirect anti-species format). TDX1779 and TDX1780 were coupled to carboxy beads and incubated against serum from *R. rickettsii* experimentally infected canines (Dog 1 or Dog 6) (Post infection day=PID). Detection of the antibody binding was reported using biotinylated Rabbit anti canine IgG.

FIG. 7 shows a schematic of the direct assay format in which anti-*R. rickettsii* antibodies are captured by PDX7 conjugated to amino beads and detected by biotinylated PDX7 peptide instead of biotinylated anti-species antibody.

FIG. 8 shows a PDX7 peptide conjugated to amino beads and screened against 574 samples from the United States using a direct assay format in which biotinylated peptide is used as the detector in place of the anti-species IgG (direct format, see FIG. 7). Using this approach, 8 positive samples were identified out of 574 tested. The 8 positives were further evaluated using an RMSF Immunofluorescent assay (IFA) for confirmation of positivity. Of the 8 PDX7 positive samples identified by multiplex, six were confirmed positive by IFA, suggesting strong sensitivity and predictive value of PDX7 peptide for capturing anti-*Rickettsia* antibodies.

FIG. 9 shows reactivity of serum from *R. rickettsii* experimentally infected canines to PDX21 polypeptides.

DETAILED DESCRIPTION

The shell vial technique is currently the most definitive diagnostic method for RMSF. This technique involves inoculating a clinical specimen onto a cell monolayer grown on a cover slip in a shell vial culture tube, low speed centrifugation to enhance viral infectivity, and then incubation. This technique, however, has serious drawbacks. Approximately one-third of the isolates can be lost when passaged to new cells. Furthermore, the culture technique is limited to laboratories equipped with biosafety level 3 facilities and staff capable of maintaining living host cells (animal mouse models or embryonated eggs), or cell cultures (Vero, L929, HEL, XTC-2, or MRC5 cells).

The standard serologic test for diagnosis of RMSF is an indirect immunofluorescence assay (IFA) for immunoglobulin G (IgG) using *R. rickettsii* pathogens fixed to slides. This assay, however, is not specific for *R. rickettsii*. It also detects, for example, *R. akari, R. parkeri*, and *Rickettsia* 364D. Cross-reactivity among antigens of pathogens within the same genus and occasionally in different genera is a known major limitation of serology. IFAs also suffer from non-specific signal as a result of antibody cross reactivity and/or anti-species antibody non-specifically binding the slides. As a further limitation, in areas where no *Rickettsia* pathogens have previously been isolated or detected, IFA assays cannot be relied upon as a sole method of diagnosis, but only as a cross reference technique.

Polymerase chain reaction (PCR) assays and sequencing methods can also be used to detect and identify RMSF in blood and skin biopsies. Though PCR and sequencing methods are rapid, traditional PCR has poor sensitivity for detecting *R. rickettsii* in blood samples and samples can be contaminated. A nested PCR assay, such as the proposed "suicide PCR" assay, attempts to mitigate vertical contaminations by amplicons from previous assays. The suicide PCR assay uses single-use primers targeting a gene never amplified previously in the laboratory. Nevertheless, standard nested PCR assays are highly subject to contamination and false-positive results.

A diagnostic method for RMSF that can specifically detect *Rickettsia rickettsii* and not cross-react with other *Rickettsia* species would contribute to rapid and accurate diagnosis of RMSF. A diagnostic test that offered such advantages while mitigating the drawbacks of culture, IFA, and PCR methods would ensure more accurate and timely diagnosis of RMSF in a larger portion of the global population. A faster and more accurate diagnostic test for RMSF would relay into earlier treatment, which is important as mortality rates for RMSF increase when treatment is delayed.

Provided herein are compositions and methods for detection and treatment of RMSF. The compositions can specifically detect *Rickettsia rickettsii* and do not likely cross-react with other *Rickettsia* species providing rapid and accurate diagnosis of RMSF.

Polypeptides

A polypeptide is a polymer where amide bonds covalently link three or more amino acids. A polypeptide can be post-translationally modified. A purified polypeptide is a polypeptide preparation that is substantially free of cellular material, other types of poly peptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or less of other polypeptides, culture medium, chemical precursors, and/or other chemicals used in synthesis. Therefore, a purified polypeptide is about 70%, 80%, 90%, 95%, 99% or more pure.

The term "polypeptides" can refer to one or more types of polypeptide or a set of polypeptides. "Polypeptides" can also refer to mixtures of two or more different types of polypeptides including, but not limited to, full-length proteins, truncated polypeptides, or polypeptide fragments. The term "polypeptides" or "polypeptide" can each mean "one or more polypeptides."

SCA2 Polypeptides

The *Rickettsia* SCA2 protein is one of 17 surface cell antigen (SCA) proteins. Surface cell antigen (SCA) proteins refer to the family of *Rickettsia* autotransporters (ATs). These SCA proteins are involved in bacterial infection of the host cell. The SCA2 protein is highly conserved across *Rickettsia* species and is an outer membrane protein that can facilitate adhesion invasion and motility of *Rickettsia* with target cells. Examples of the polypeptide sequence of SCA2 is shown in GenBank Accession number AJG33947.1 and AJG32613.1. SCA2 functions, for example, as a formin mimic that is responsible for actin-based motility of *Rickettsia* in the host cell cytosol.

A stretch of amino acids that is only present in *R. rickettsii* strains exists in the autochaperone domain (AC) of the extracellular protein SCA2. The entire unique region called PDX6 herein, while a slightly truncated region is named PDX7 herein. See FIG. 3. Additionally, two recombinant fusion proteins have been constructed, TDX1779 and TDX1780, by fusion of 3 PDX6 repeats or 5 PDX6 repeats, respectively. Any of these polypeptides can be immobilized to a support such as, for example, barcoded magnetic beads (BMBs) and used in a detection assay.

(PDX6)
SEQ ID NO: 1
<u>C</u>DYKKSLLXLRSSDEDDQGYATGYTTDEEELEEXNSTTGEELKKDISD

The X at position 9 can be E or A. The X at position 34 can be G or S.

(PDX7)
SEQ ID NO: 2
<u>C</u>SSDEDDQGYATGYTTDEEELEEXNSTTGEELKKDISD

The X at position 24 can be G or S.

(TDX1779)
SEQ ID NO: 3
<u>MDWTWRVFFLLALATGVHS</u><u>C</u>DYKKSLLELRSSDEDDQGYATGYTTDEE

ELEESNSTTGEELKKDISDDYKKSLLELRSSDEDDQGYATGYTTDEEE

LEESNSTTGEELKKDISDDYKKSLLELRSSDEDDQGYATGYTTDEEEL

EESNSTTGEELKKDISD<u>AAAHHHHHHHH</u>

The structure of TDX1779 is (MDWTWRVFFLLA-LATGVHS-PDX6-PDX6-PDX6-8×HIS) (see FIG. 3). The underlined portion of the sequence at the N terminus (e.g., MDWTWRVFFLLALATGVHS SEQ ID NO:24) is a secretory (signal) sequence. The "8×HIS" means a His tag comprising 8 His residues is present.

(TDX1780)
SEQ ID NO: 4
<u>MDWTWRVFFLLALATGVHS</u><u>C</u>DYKKSLLELRSSDEDDQGYATGYTTDEE

ELEESNSTTGEELKKDISDDYKKSLLELRSSDEDDQGYATGYTTDEEE

LEESNSTTGEELKKDISDDYKKSLLELRSSDEDDQGYATGYTTDEEEL

EESNSTTGEELKKDISDDYKKSLLELRSSDEDDQGYATGYTTDEEELE

ESNSTTGEELKKDISDDYKKSLLELRSSDEDDQGYATGYTTDEEELEE

SNSTTGEELKKDISD<u>AAAHHHHHHHH</u>

The structure of TDX1780 is (MDWTWRVFFLLA-LATGVHS-PDX6-PDX6-PDX6-PDX6-PDX6-PDX6-8× HIS). See FIG. 3.

The underlined amino acids indicate non-natural variation and/or additions to the polypeptide sequence that were engineered for biochemical/immunological purposes. These polypeptides are therefore non-naturally occurring and have different properties than naturally occurring polypeptides including, for example, better purification properties and better specificity and sensitivity in assays.

A secretory signal sequence is a peptide sequence (or polynucleotide encoding the peptide sequence) present at the N-terminus (or in some cases, the C-terminus) of a peptide sequence. A secretory signal sequence can be referred to by various names such as, but not limited to, a signal sequence, a targeting signal, a localization signal, a localization sequence, a transit peptide, a leader sequence, a leader peptide, a prepro sequence, a pre sequence, or a secretory signal peptide). A secretory signal sequence can be about 10 to 110 amino acids long (e.g., about 10, 15, 20, 25, 30, 35, 40, 45, 50, 55, 60, 65, 70, 75, 80, 85, 90, 95, 100, 105 or 110 amino acids long). A secretory signal sequence, as a component of a larger polypeptide, can be useful for targeting and can direct the larger polypeptide through a secretory pathway of a cell in which it is synthesized. In some embodiments, the larger polypeptide is cleaved to remove the secretory signal sequence during transit through the secretory pathway. A secretory signal sequence can be endogenous or engineered.

A secretory signal sequence can be synthesized according to the rules established, for example, by von Heinje (Eur. J. Biochem. 133: 17-21, 1983; J. Mol. Biol. 184: 99-105, 1985; Nuc. Acids. Res. 14: 4683-3690, 1986). Examples of secretory signal sequences are shown in Table 2. Any secretory signal sequence known in the art or to those of ordinary skill in the art can be used in the polypeptides and methods described herein.

TABLE 2

| Description (if applicable) | A secretory signal sequence | SEQ ID NO: |
|---|---|---|
| TDX1779 and TDX1780 secretory signal sequence | MDWTWRVFFLLALATGVHS | SEQ ID NO: 24 |
| SignalP 3.0 | MDWTWRILFLVAAATGTHA | SEQ ID NO: 25 |
| *Erwinia carotovora* pectate lyase 2 (pelB) leader peptide | MKYLLPTAAAGLLLLAAQPAMA | SEQ ID NO: 26 |
| Human growth hormone signal sequence | MATGSRTSLLLAFGLLCLWLQEGSA | SEQ ID NO: 27 |
| otPA pre-pro signal sequence | MPLLLLLPLLWAGALA | SEQ ID NO: 28 |
| Human CD33 signal sequence | MDAMKRGLCCVLLLCGAVFVSLSQEIHAELRRFRR | SEQ ID NO: 29 |
| PhoA | MKQSTIALALLPLLFTPVKTA | SEQ ID NO: 30 |
| OmpA | MKKTAIAIAVALAGFATVAQA | SEQ ID NO: 31 |
| DsbA | MKKIWLALAGLVLAFSASA | SEQ ID NO: 32 |
| TorT | MRVLLFLLSLFMLPAFS | SEQ ID NO: 33 |
| SufI | MSLSRRQFIQASGIALCAGAVPLKASA | SEQ ID NO: 34 |
| TorA | MNNNDLFQASRRRFLAQLGGLTVAGMLGPSLLTPRRATA | SEQ ID NO: 35 |
| N terminal secretory signal peptide sequence | MAGPATQSPMKLMALQLLLWHSALWTVQEA | SEQ ID NO: 36 |
| human α-1-anti trypsin (AAT) | MMPSSVSWGILLLAGLCCLVPVSLA | SEQ ID NO: 37 |
| human Factor IX (FIX) | MQRVNMIMAESPSLITICLLGYLLSAECTVFLDHENANKILNRPKR | SEQ ID NO: 38 |
| human Prolactin (Prolac) | MKGSLLLLLVSNLLLCQSVAP | SEQ ID NO: 39 |
| human Albumin (Alb) | MKWVTFISLLFLFSSAYSRGVFRR | SEQ ID NO: 40 |
| YDR420w secretory signal peptide | MVSLKIKKLLLVSLLNAIEAYSNDTIYSTSYNNGIESTPSYSTSAISSTGSSNKENAITSSSETTTMAGDYGESGSTTIMDEQETGTSSQYISVTTTTQ | SEQ ID NO: 41 |
| YBR187w secretory signal peptide | NGGNMAIKKASLIALLPLFTAAAAAATDAETSNESGSSSHLKS | SEQ ID NO: 42 |
| YHR139c secretory signal peptide | MKFTSVLAFFLATLTASATFLYKRQNVTSGGGTVPIITGGPAVSGSQSNVTTTLFNSTSTLNITQLYQIATDVNDTLQSESSS | SEQ ID NO: 43 |
| YGR014w secretory signal peptide | MQFPFACLLSTLVISGSLARASPFDFIFGNGTQQAQSQSESQGQVSFTNEASQDSSTTSLVTAYSQGVHSHQSATIVSATISSLPSTWYDASSTSQTSVS | SEQ ID NO: 44 |

TABLE 2-continued

| Description (if applicable) | A secretory signal sequence | SEQ ID NO: |
|---|---|---|
| YBR078w secretory signal peptide | MQFKNALTATAILSASALAANSTTSIPSSCSIG TSATATAQADLDKISQCSTIVGNLTITGDLGSA ALASIQEIDGSLTIFNSSSLSSFSADIKKI | SEQ ID NO: 45 |
| YNL300w secretory signal peptide | MKFSTLSTVAAIAAFASADSTSDGVTYVDVTT TPQSTTSMVSTVKTTSTPYTTSTIATLSTKSIS SQANTTTHEIST | SEQ ID NO: 46 |
| YLR084c secretory signal peptide | MFVHRLWTLAFPFLVEISKASQLENIKSLLDI EDNVLPNLNISQNNSNAVQILGGVDALSFYEY TGQQNFTKEIGPETSSHGLVYYSNNTYIQLED ASDD | SEQ ID NO: 47 |
| YMR008c secretory signal peptide | MKLQSLLVSAAVLTSLTENVNAMSPNNSYVP ANVTCDDDINLVREASGLSDNEYEMLKKRDA YTKE | SEQ ID NO: 48 |

A polypeptide can comprise about 70%, 75%, 80%, 85%, 90%, 95%, 96%, 97%, 98%, 99% or more sequence identity to one or more polypeptides (e.g., 1, 2, 3, 4, 5, 6, 7, or more) as set forth in SEQ ID NO:1, 2, 3, 4, 5, 6, or 7 (see description of SEQ ID NOs:5, 6, and 7 below) and can further comprise one or more (e.g., 1, 2, 3, 4, 5, or more) secretory signal sequences, one or more (e.g., 1, 2, 3, 4, 5, or more) epitope tags, or one or more secretory signal sequences and one or more epitope tags. These elements can be present as a fusion protein with one or more linkers between the individual proteins or sequences making up the fusion protein. Alternatively, no linkers can be present between the individual proteins or sequences making up the fusion protein. The elements of the fusion protein (i.e., a polypeptide as set forth in SEQ ID NO:1, 2, 3, 4, 5, 6, or 7, secretory signal sequences, and epitope tags) can occur in any order in the fusion protein.

VUT Polypeptides

The *Rickettsia* vitamin uptake transporter VUT family protein is a 200 amino acid, hypothetical protein, predicated to reside on the bacterial cell surface. The proposed function of VUT based on domain homology is consistent with queuosine salvage, a critical requirement for bacterial growth. An example of this protein is GenBank Accession number WP 012150928.1, which is shown in SEQ ID NO:8:

```
MLFDKIKSKRKGKCMSNINAKFYIPLVSLLGVFIYLLNCFNKISQCSL

VFVFLAITTNIISELYGRKRALIAVALCIIVSFGLLWNFNYYIHGRVI

KGVVFASFVSVLLSTYCSTSIFSQLKPRCSLNTRNFASLIMCAVVDGI

VMSGFFVNVFSTSKVLSIFYKEVLYKCAYSLTVYICIFLVQKVYGNNG

SVRALKNF
```

In one embodiment, the VUT protein has two regions of interest flanking either end of the protein. PDX21 and PDX39 peptides were derived from the first 38 and last 38 residues, respectively, of the VUT protein. In one embodiment, the PDX21 and PDX39 peptides have point mutations in the cysteine residues. That is, naturally occurring cysteine amino acids are changed to, for example, serine. Furthermore, a naturally occurring methionine can be changed to a cysteine. These changes are underlined below.

(PDX21)

SEQ ID NO: 5

MLFDKIKSKRKGK<u>S</u>MSNINAKFYIPLVSLLGVFIYLLN (PDX39)

SEQ ID NO: 6

<u>C</u>KEVLYK<u>S</u>AYSLVYI<u>S</u>IFLVQKVYGNNGSVRALKNF (PDX40)

SEQ ID NO: 7

<u>C</u>LFDKIKSKRKGK<u>S</u>MSNINAKFYIPLVSLLGVFIYLLN

PDX40 is PDX21 with the first methionine (M) replaced with cysteine (C) for biochemistry purposes.

These polypeptides are therefore non-naturally occurring and have different properties than naturally occurring polypeptides including, for example, a reduced tendency to form secondary structures and the ability to conjugate to solid phases for testing.

One embodiment provides a purified polypeptide comprising the complete SCA2 protein, the complete VUT protein, PDX6, PDX7, TDX1779, TDX1780, PDX21, PDX39, PDX40 or a fragment thereof. A polypeptide fragment of the complete SCA2 protein, the complete VUT protein, PDX6, PDX7, TDX1779, TDX1780, PDX21, PDX39, PDX40 can be less than about 350, 300, 250, 200, 150, 100, 95, 90, 80, 70, 60, 50, 40, 35, 30, 25, 20, 15, 10 (or any range between about 10 and about 350) total contiguous amino acids. In one embodiment a polypeptide fragment is more than about 10, 15, 20, 25, 30, 35, 40, 50, 60, 70, 80, 90, 95, 100, 150, 200, 250, 300, or 350 total contiguous amino acids of the complete SCA2 protein, the complete VUT protein, PDX6, PDX7, TDX1779, TDX1780, PDX21, PDX39, PDX40. In an embodiment, a polypeptide has less than about 95, 75, 50, or 25 total amino acids and comprises 70%, 80%, 90%, 95% or more sequence identity to a polypeptide as set forth in SEQ ID NO:1, 2, 5, 6, or 7. In an embodiment a polypeptide has less than about 400, 350, 300, 200, or 150 total amino acids and comprises about 70%, 80%, 90%, 95% or more sequence identity to a polypeptide as set forth in SEQ ID NO:3 or 4.

For example, SEQ ID NO:1 is 48 amino acids in length. In an embodiment, the polypeptide can comprise additional amino acids to extend the polypeptide to a length of, for example 95 amino acids. The extra or additional amino acids can be, for example, labels, tags, additional *R. rickettsii* amino acids, amino acids unrelated to *R. rickettsii*, amino acids that can be used for purification, amino acids that can be used to increase solubility of the polypeptide, amino acids to improve other characteristics of the polypeptide, or other amino acids. In an embodiment, the additional amino acids are not R. rickettsii amino acids. In this example, the 95 amino acid long polypeptide has about 70%, 80%, 90%, 95% or more sequence identity to a polypeptide as set forth in SEQ ID NO:1 over the 48 consecutive amino acids of SEQ ID NO:1, while the remaining 47 amino acids of the 95 amino acid polypeptide can have, e.g., no sequence identity to SEQ ID NO:1.

In another non-limiting example, a polypeptide having less than 75 total amino acids and comprising 90% or more sequence identity to a polypeptide as set forth in SEQ ID NO:2 can be a polypeptide having 70 amino acids. The 70 amino acid long polypeptide can have 90% or more sequence identity to the polypeptide as set forth in SEQ ID NO:2 over the 38 consecutive amino acids of SEQ ID NO:2, while the remaining 32 amino acids of the 70 amino acid polypeptide can have, e.g., no sequence identity to SEQ ID NO:2.

In another non-limiting example, a polypeptide having less than 350 total amino acids and comprising 90% or more sequence identity to a polypeptide as set forth in SEQ ID NO:3 can be 300 amino acids in length. The 300 amino acid long polypeptide can have 90% or more sequence identity to the polypeptide as set forth in SEQ ID NO:3 over the 172 consecutive amino acids of SEQ ID NO:3, while the remaining 128 amino acids of the 300 amino acid polypeptide can have, e.g., no sequence identity to SEQ ID NO:3.

The fact that a polypeptide (e.g., SEQ ID NOs:1-7) is smaller than a full length a R. rickettsii polypeptide can be important because smaller polypeptides can have greater specificity and/or sensitivity than full length polypeptides in detection or diagnostic assays. Additionally, these smaller polypeptides can be less expensive to manufacture and can be obtained at greater purity than full length polypeptides.

In one embodiment, a polypeptide or fragment thereof is non-naturally occurring. That is, a polypeptide or fragment comprises 1, 2, 3, 4, 5, 10, 20, 30, 40, 50, 75 or more non-naturally occurring amino acids. In an embodiment, the non-naturally occurring amino acids can provide a beneficial property such as increased solubility of the polypeptide or increased sensitivity or increased specificity of the polypeptide in assays.

The terms "sequence identity" or "percent identity" are used interchangeably herein. To determine the percent identity of two polypeptide molecules or two polynucleotide sequences, the sequences are aligned for optimal comparison purposes (e.g., gaps can be introduced in the sequence of a first polypeptide or polynucleotide for optimal alignment with a second polypeptide or polynucleotide sequence). The amino acids or nucleotides at corresponding amino acid or nucleotide positions are then compared. When a position in the first sequence is occupied by the same amino acid or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). In some embodiments the length of a reference sequence (e.g., SEQ ID NOs:1-7) aligned for comparison purposes is at least 50, 60, 70, or 80% of the length of the comparison sequence, and in some embodiments is at least 90% or 100%. In an embodiment, the two sequences are the same length.

Ranges of desired degrees of sequence identity are approximately 80% to 100% and integer values in between.

Percent identities between a disclosed sequence and a claimed sequence can be at least 80%, at least 83%, at least 85%, at least 90%, at least 95%, at least 98%, at least 99%, at least 99.5%, or at least 99.9%. In general, an exact match indicates 100% identity over the length of the reference sequence (e.g., SEQ ID NOs: 1-7).

Polypeptides that are sufficiently similar to polypeptides described herein (e.g., SCA2 or VUT polypeptides) can be used herein. Polypeptides that are about 90, 91, 92, 93, 94 95, 96, 97, 98, 99, 99.5% or more identical to polypeptides described herein can also be used herein.

A polypeptide variant differs by about, for example, 1, 2, 3, 4, 5, 6, 7, 8, 9, 10, 20, 30, 40, 50, 60, 70, 80, 90, or more amino acid residues (e.g., amino acid additions, substitutions, or deletions) from a peptide shown SEQ ID NOs:1-7 or a fragment thereof. Where this comparison requires alignment, the sequences are aligned for maximum homology. The site of variation can occur anywhere in the polypeptide. In one embodiment, a variant has about 70%, 75%, 80%, 85%, 90%, 95%, 96%, 97%, 98%, 99% sequence identity to the original polypeptide.

Variant polypeptides can generally be identified by modifying one of the polypeptide sequences described herein and evaluating the properties of the modified polypeptide to determine if it is a biological equivalent. A variant is a biological equivalent if it reacts substantially the same as a polypeptide described herein in an assay such as an immunohistochemical assay, an enzyme-linked immunosorbent assay (ELISA), a turbidimetric immunoassay, a particle-enhanced turbidimetric immunoassay, a particle-enhanced turbidimetric immunoassay, a radioimmuno-assay (RIA), immunoenzyme assay, a western blot assay, or other suitable assay. In other words, a variant is a biological equivalent if it has 90-110% of the activity of the original polypeptide. In one embodiment, the assay is a competition assay wherein the biologically equivalent polypeptide is capable of reducing binding of the polypeptide described herein to a corresponding reactive antigen or antibody by about 80%, 95%, 99%, or 100%. An antibody that specifically binds a corresponding polypeptide also specifically binds the variant polypeptide.

Variant polypeptides can have one or more conservative amino acid variations or other minor modifications and retain biological activity, i.e., are biologically functional equivalents to PDX6, PDX7, TDX1779, TDX1780, PDX21, PDX39, PDX40 or a fragment thereof. Variant polypeptides can have labels, tags, additional R. rickettsii amino acids, amino acids unrelated to R. rickettsii, amino acids that can be used for purification, amino acids that can be used to increase solubility of the polypeptide, amino acids to improve other characteristics of the polypeptide, or other amino acids. In an embodiment, the additional amino acids are not R. rickettsii amino acids.

Methods of introducing a mutation into an amino acid sequence are well known to those skilled in the art. See, e.g., Ausubel (ed.), Current Protocols in Molecular Biology, John Wiley and Sons, Inc. (1994); Maniatis et al., Molecular Cloning: A Laboratory Manual, Cold Spring Harbor laboratory, Cold Spring Harbor, N.Y. (1989). Mutations can also be introduced using commercially available kits such as "QuikChange™ Site-Directed Mutagenesis Kit" (Stratagene). The generation of a functionally active variant polypeptide by replacing an amino acid that does not influence the function of a polypeptide can be accomplished by one skilled in the art. A variant polypeptide can also be chemically synthesized.

Variant polypeptides can have conservative amino acid substitutions at one or more predicted nonessential amino acid residues. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. In one embodiment a polypeptide has about 1, 2, 3, 4, 5, 10, 20 or fewer conservative amino acid substitutions.

A polypeptide can be a fusion protein, which can contain other amino acid sequences, such as amino acid linkers, amino acid spacers, signal sequences, TMR stop transfer sequences, transmembrane domains, as well as ligands useful in protein purification, such as glutathione-S-transferase, histidine tag (e.g., about 6, 7, 8, 9, 10, or more His residues), and staphylococcal protein A, or combinations thereof. In an embodiment, a polypeptide comprises one or more epitope tags, such as FLAG (for example, DYKDDDDK; SEQ ID NO:16), HA (YPYDVPDYAC; SEQ ID NO:9), myc (EQKLISEEDLC; SEQ ID NO:10), V5 (GKPIPNPLLGLDST; SEQ ID NO:11), E-tag (GAPVPYPDPLEPR; SEQ ID NO:12), VSV-g (YTDIEMNRLGK; SEQ ID NO:13), 6×His (HHHHHH; SEQ ID NO:14), and HSV (QPELAPEDPEDC; SEQ ID NO:15). An antibody, such as a monoclonal antibody, can specifically bind to an epitope tag and be used to purify a polypeptide comprising the epitope tag.

A fusion protein can comprise two or more different amino acid sequences operably linked to each other. A fusion protein construct can be synthesized chemically using organic compound synthesis techniques by joining individual polypeptide fragments together in fixed sequence. A fusion protein can also be chemically synthesized. A fusion protein construct can also be expressed by a genetically modified host cell (such as E. coli) cultured in vitro, which carries an introduced expression vector bearing specified recombinant DNA sequences encoding the amino acids residues in proper sequence. The heterologous polypeptide can be fused, for example, to the N-terminus or C-terminus of a polypeptide. More than one polypeptide can be present in a fusion protein. Fragments of polypeptides can be present in a fusion protein. A fusion protein can comprise, e.g., one, two, three, four, five, six, seven or more of PDX6, PDX7, TDX1779, TDX1780, PDX21, PDX39, PDX40, fragments thereof, or combinations thereof. Polypeptides can be in a multimeric form. In other words, a polypeptide can comprise two or more copies (e.g., two, three, four, five, six, seven or more) of PDX6, PDX7, TDX1779, TDX1780, PDX21, PDX39, PDX40, fragments thereof, or a combination thereof. A polypeptide can include, e.g., a fusion protein of two, three, four, five, six, seven or more polypeptides having about 70%, 75%, 80%, 85%, 90%, 95%, 96%, 97%, 98%, 99% or more sequence identity to SEQ ID NO:1, 2, 3, 4, 5, 6, or 7; or a fusion protein of at least two polypeptides having about 70%, 75%, 80%, 85%, 90%, 95%, 96%, 97%, 98%, 99% sequence identity to SEQ ID NO:1, 2, 3, 4, 5, 6, or 7. A polypeptide can be a fusion protein that can include one or more linkers between the individual proteins making up the fusion protein (i.e., SEQ ID NO:1, 2, 3, 4, 5, 6, or 7). Alternatively, no linkers can be present between the individual proteins making up the fusion protein. A fusion polypeptide can contain other amino acid sequences, such as amino acid linkers, amino acid spacers, signal sequences, TMR stop transfer sequences, transmembrane domains, as well as ligands useful in protein purification, such as glutathione-S-transferase, histidine tag, epitope tags, and staphylococcal protein A, or combinations thereof.

A still further component of a fusion protein can be a secretory (signal) sequence. These sequences can allow for secretion of the fusion protein from the host cell during expression. The secretory (signal) sequence can be that of the heterologous protein being produced, if it has such a sequence, or can be derived from another secreted protein (e.g., t-PA), or synthesized de novo. The polynucleotide sequence encoding the secretory (signal) sequence can be operably linked to fusion protein DNA sequence, i.e., the two sequences are joined in the correct reading frame and positioned to direct the newly synthesized polypeptide into the secretory pathway of the host cell. Polynucleotide sequences encoding secretory (signal) sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

In an embodiment a polypeptide as described herein is present in an immunocomplex with one or more antibodies or specific binding fragments thereof that specifically bind to a polypeptide as set forth in SEQ ID NO:1, 2, 3, 4, 5, 6, or 7. The one or more antibodies or specific binding fragments thereof can be anti-R. rickettsii antibodies or specific binding fragments thereof.

Polypeptides can be lyophilized, desiccated, or dried, for example freeze-dried. A lyophilized polypeptide can be obtained by subjecting a preparation of the polypeptides to low temperatures to remove water from the sample. A desiccated polypeptide composition can be obtained by drying out a preparation of the polypeptides by removal of water. A dried polypeptide preparation can refer to a polypeptide preparation that has been air dried (e.g., lyophilized).

Labels

One or more polypeptides described herein (including detector polypeptides) can be conjugated to one or more labels or tags. A label or tag can be coupled directly or indirectly to the desired component of the assay (e.g., an antibody, polypeptide, or support). For example, polypeptides can be conjugated to a fluorophore, an enzyme, a chemiluminescent moiety, a radioactive moiety, an organic dye, a small molecule, a polypeptide or functional fragment thereof. Examples of fluorophores include fluorescent dyes like phycoerytherin (PE), fluorescein isothiocyanate (FITC), tetramethylrhodamine (TRITC), BODIPY, Texas red, rhodamine and AlexaFluor® dyes. Fluorescent dyes can also comprise fluorescence resonance energy transfer (FRET)-dyes or time-resolved (TR)-FRET dyes. Fluorophore labels can comprise fluorescent proteins such as green fluorescent protein (GFP), enhanced green fluorescent protein, and cyan fluorescent protein (CFP). Examples of enzyme labels include hydrolases, such as phosphatases including alkaline phosphatase, esterases and glycosidases, or oxidoreductases, peroxidases such as horseradish peroxidase, and others commonly used in enzyme-linked immunosorbent assays, ELISAs. When a substrate such as 3,3'5,5'-Tetramethylbenzidine (TMB), 3,3'-Diaminobenzidene (DAB), or 2,2'-azinobis(3-ethylbenzothiazoline-6-sulphonic acid) (ABTS) are applied to HRP, a colored (chromogenic) or light (chemiluminescent) signal is produced. Radioactive moiety labels can be, for example, $^{3}H$, $^{125}I$, $^{35}S$, $^{14}C$, or $^{32}P$. Small molecule labels include, for example, resins such as agarose beads and magnetic beads such as fluorescently labeled magnetic beads or barcoded magnetic beads (e.g., barcoded magnetic beads available from Applied BioCode of Santa Fe Springs, CA), Dynabeads™, colored glass or plastic (e.g., polystyrene, polypropylene, latex, etc.) beads, and nanoparticles such as colloidal gold. Polypeptide or functional fragment labels include, for example, avidin, streptavidin or NeutrAvidin, which have an affinity for biotin, hemagglutinin (HA), glutathione-S-transferase (GST), or c-myc.

Detection of labels or tags can be done using many different methods. For example, a radioactive label can be detected using a scintillation counter, photographic film as in autoradiography, or storage phosphor imaging. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Simple colorimetric labels can be detected by observing the color associated with the label. When pairs of fluorophores are used in an assay, they may have distinct emission patterns (wavelengths) so that they can be easily distinguished.

While components described herein (e.g., polypeptides, antibodies and specific binding fragments thereof) can comprise a label, a label is not necessary for detection of polypeptide/antibody complexes since many options exist for label-free detection including, for example surface plasmon resonance, bio-layer interferometry, and grating-coupled interferometry detection assays.

Supports

In an embodiment, a component of an assay (e.g., a polypeptide or antibody or specific binding fragment thereof) can be immobilized to a support. A support is any material that is appropriate for or that can be modified to be appropriate for attachment of one or more polypeptides, antibodies, or specific binding fragments as described herein. Examples of supports include glass and modified or functionalized glass, plastics (including acrylics, polystyrene, methylstyrene, polyurethanes, Teflon®, etc.), paramagnetic materials, thoria sol, carbon graphite, titanium oxide, latex or cross-linked dextrans such as Sepharose, cellulose polysaccharides, nylon or nitrocellulose, ceramics, resins, silica or silica-based materials including silicon and modified silicon, carbon metals, inorganic glasses, optical fiber bundles, and a variety of other polymers. In an embodiment a support can be located in a microtiter well plate (e.g., a 96-well, 384-well or 1536-well plate). In an embodiment, a support can be located within a flow cell or flow cell apparatus (e.g., a flow cell on a protein chip). A support can be a solid support.

In an embodiment, a support can be a bead such as a magnetic barcoded bead, microsphere, particle, membrane, chip, slide, well, or test tube. Beads include microspheres or particles, which can be small, discrete, non-planar particles in the micrometer or nanometer dimensions. A bead can be spherical or irregular. A bead can be porous. In an embodiment, a support can comprise a patterned surface suitable for immobilization of polypeptides in an ordered pattern (e.g., a protein chip).

In an embodiment one or more polypeptides as described herein can be immobilized to a support via a linker molecule. One or more polypeptides can be conjugated to a support using any suitable methodology. In an embodiment one or more polypeptides are conjugated to a support using a conjugation reagent, including covalent and non-covalent conjugation reagents. Covalent conjugation reagents can include any chemical or biological reagent that can be used to covalently immobilize a polypeptide on a surface. Covalent conjugation reagents include, for example, a carboxyl-to-amine reactive group such as carbodiimides such as EDC or DCC, an amine reactive group such as N-hydroxysuccinimide (NHS) ester or imidoesters, a sulfhydryl-reactive crosslinker such as maleimides, haloacetyls, or pyridyl disulfides, carbonyl-reactive crosslinker groups such as, hydrazides or alkoxyamines, a photoreactive crosslinker such as aryl azides or dizirines, or a chemoselective ligation group such as a Staudinger reaction pair. Non-covalent immobilization reagents can include any chemical or biological reagent that can be used to immobilize a polypeptide non-covalently on a surface, such as affinity tags such as biotin or capture reagents such as streptavidin or anti-tag antibodies, such as anti-His6 or anti-Myc antibodies.

Methods of Detection and Diagnosis

In an embodiment an assay method can comprise contacting a test sample with one or more polypeptides under conditions suitable for formation of complexes between polypeptides and antibodies or specific binding fragments thereof. The one or more polypeptides can comprise, for example, about 70%, 75%, 80%, 85%, 90%, 95%, 96%, 97%, 98%, 99% sequence identity to SEQ ID NO:1, 2, 3, 4, 5, 6, or 7, fragments, or variants of these polypeptides as described herein. Complexes of polypeptides and antibodies or specific binding fragments thereof can be detected. In an embodiment, complexes of polypeptides and antibodies or specific binding fragments can also comprise one or more labels or tags. If complexes are detected, then the sample contains anti-*Rickettsia rickettsii* antibodies.

In an embodiment, a method comprises diagnosing a disease caused by *Rickettsia rickettsii* in a subject. A test sample can be contacted with one or more polypeptides comprising about 70%, 75%, 80%, 85%, 90%, 95%, 96%, 97%, 98%, 99% sequence identity to SEQ ID NO:1, 2, 3, 4, 5, 6, or 7, fragments, or variants as described herein. Complexes of anti-*Rickettsia rickettsii* antibodies or specific binding fragments thereof and the one or more polypeptides are then detected. The subject can have been infected with *Rickettsia* for less than about 14, 13, 12, 11, 10, 9, 8, 7, 6, 5, 4, 3, or 2 days. The amount of anti-*Rickettsia rickettsii* antibodies or specific binding fragments thereof in the sample can be determined. The amount of the complexes in the sample can be compared to a control sample or control standard, wherein elevated levels of the complexes as compared to the control sample or control standard is an indication of a disease caused by *R. rickettsii*. Where the complexes are detected a treatment can be administered to the subject. A subject can be human or a non-human mammal, such as a dog, horse, cow, or cat. A test sample can be, for example, blood, plasma, serum, lymph fluid, or any other body fluid sample.

In an embodiment specific binding between one or more polypeptides described herein and one or more anti-*Rickettsia rickettsii* antibodies or specific binding fragments thereof are detected using a secondary antibody or a specific binding fragment thereof. In an example, a secondary antibody can be used to detect the specific binding. For example, a secondary antibody or specific binding fragment thereof is capable of binding the anti-*Rickettsia rickettsii* antibodies or specific binding fragments thereof. In an embodiment a secondary antibody is an anti-species antibody such as a rabbit anti-dog or rabbit anti-human antibody. In an embodiment, the secondary antibody is covalently or non-covalently bound to a label or tag that can be used for detection of polypeptide/anti-*Rickettsia rickettsii* antibody/secondary antibody complex. In one example, a secondary antibody can be conjugated to biotin or other label or tag. A streptavidin conjugate (in the case of a biotin label), such as streptavidin fluorochrome conjugate, can be used to detect the polypeptide/anti-*Rickettsia rickettsii* antibody/secondary antibody complex.

In an embodiment specific binding between one or more polypeptides described herein and one or more anti-*Rickettsia rickettsii* antibodies or specific binding fragments thereof are detected using one or more detector polypeptides that specifically bind anti-*Rickettsia rickettsii* antibodies or specific binding fragments thereof. In an example, the one or more detector polypeptides comprise about 70%, 75%, 80%, 85%, 90%, 95%, 96%, 97%, 98%, 99% sequence identity to a polypeptide as set forth in SEQ ID NO:1, 2, 3, 4, 5, 6, or 7, fragments thereof, or variants as described herein. In an embodiment, the one or more detector polypeptides are covalently or non-covalently bound to a label or tag that can be used for detection of polypeptide/anti-*Rickettsia rickettsii* antibody/detector polypeptide complex. In one example, a detector polypeptide can be conjugated to a label or tag such as biotin. A streptavidin conjugate (in the case of a biotin label), such as streptavidin fluorochrome conjugate can be used to detect the polypeptide/anti-*Rickettsia rickettsii* antibody/detector polypeptide complex.

The detection of specific binding between one or more polypeptides described herein and one or more antibodies or specific binding fragments thereof can be completed using any suitable method, for example, an immunoassay such as a competitive immunoassay, a sandwich immunoassay, an enzyme-linked immunosorbent assay (ELISA), an immunohistochemical assay, a turbidimetric immunoassay, a particle-enhanced turbidimetric immunoassay, a radioimmunoassay (RIA), a fluorescent immunosorbent assay (FIA), a multiplex immunoassay, a protein/peptide array immunoassay, a solid phase radioimmunoassay (SPRIA), an indirect immunofluorescence assay (IIF), a chemiluminescent immunoassay (CIA), a particle based multianalyte test (PMAT), a dot blot assay, or a western blot assay. Other assay methods that can be used to detect antibodies and/or antibody/polypeptide complexes include, for example surface plasmon resonance (SPR), isothermal titration calorimetry (ITC), microscale thermophoresis (MST), biolayer interferometry, or grating-coupled interferometry.

Antibodies described herein can be a polyclonal antibody, a monoclonal antibody, a single chain antibody (scFv), or a specific binding fragment of an antibody. Antibody specific binding fragments are one or more portions of an intact antibody that comprises the antigen binding site or variable region of an intact antibody, where the portion is free of the constant heavy chain domains of the Fc region of the antibody. Examples of antibody fragments that bind to antigens include Fab, Fab', Fab'-SH, F(ab')$_2$ and Fv fragments. An antibody described herein can be any class of antibody that includes, for example, IgG, IgM, IgA, IgD and IgE.

"Specifically binds" or "specific for" means that a first antigen, e.g., a polypeptide as shown in SEQ ID NOs:1-7, fragments thereof, or variants as described herein, recognizes and binds to an anti-*R. rickettsia* antibody or specific binding fragment thereof with greater affinity than other non-specific molecules. A non-specific molecule is an antigen that shares no common epitope with the first antigen. In an embodiment, a non-specific molecule is not a *R. rickettsia* polypeptide and is not related to *R. rickettsia*. In an embodiment, a non-specific molecule is not derived from a *Rickettsia* organism. For example, an antibody raised against a first antigen (e.g., *R. rickettsia*) to which it binds more efficiently than to a non-specific antigen can be described as specifically binding to the first antigen. A polypeptide specifically binds to an anti-*R. rickettsia* antibody or specific binding fragment when it binds with a binding affinity ($K_D$) of $10^{-6}$ M or less. In an embodiment, a polypeptide specifically binds to an anti-*R. rickettsia* antibody or specific binding fragment when it binds with an affinity ($K_D$) of $2 \times 10^{-6}$ M or less. In an embodiment, a polypeptide specifically binds to an anti-*R. rickettsia* antibody or specific binding fragment when it binds with an affinity ($K_D$) of at least $10^{-6}$ M, $10^{-7}$ M, $10^{-8}$ M, $10^{-9}$ M or less. In certain embodiments, the affinity is measured by surface plasmon resonance or KinExA assay. In an embodiment, the methods specifically detect *Rickettsia rickettsii* and do not detect other *Rickettsia* species such as *R. conorii*, *R. africae*, *R. japonica*, *R. phillipii*, *R. parkeri*, *R. massiliae*, *R. felis*, *R. typhi*, *R. prowazekii*, *R. bellii*, or combinations thereof.

Kits

A kit can comprise one or more of the polypeptides described herein. A kit can also include a tag, label, or conjugate for detection. One or more polypeptides can be covalently or non-covalently immobilized on a support.

For example, a label of the kit can include a fluorophore, an enzyme, a chemiluminescent moiety, a radioactive moiety, an organic dye, a small molecule, a polypeptide or functional fragment thereof. In some embodiments, a label of the kit includes phycoerytherin. In some embodiments, a label of the kit includes fluorescein isothiocyanate. In some embodiments, a label is conjugated to a secondary antibody or detector polypeptide.

A kit can include a positive control. In some embodiments, a positive control can be a sample containing a detectable amount of anti-*R. rickettsia* antibodies. In an embodiment, a positive control can be obtained from a diseased subject who has anti-*R. rickettsia* antibodies. In an embodiment, a positive control can comprise anti-*R. rickettsia* antibodies synthesized in vitro or otherwise obtained. In an embodiment, a kit can include a negative control. A negative control can be a sample containing no detectable amount of anti-*R. rickettsia* antibodies. In some embodiments, a negative control can be obtained from a healthy control individual or can be synthesized in vitro. For example, a negative control can include water or buffer.

In some embodiments a kit can include a standard curve for determining an amount of anti-*R. rickettsia* antibodies in a sample. Anti-*Rickettsia rickettsii* antibodies can be used to create a standard curve for an assay. A standard curve can be used to determine the concentration of anti-*Rickettsia rickettsii* antibodies in a sample. A standard curve is obtained by relating a measured quantity to the concentration of the anti-*Rickettsia rickettsia* antibodies in "known" samples, i.e., standards of known concentration. These standards provide a reference to determine unknown concentrations of anti-*R. rickettsia* antibodies in a sample. The amounts of standards can span the whole range of concentrations expected to be found in the "unknown" or "test" sample concentration.

A kit can further include one or more assay reagents that facilitate binding of the one or more polypeptides to anti-*Rickettsia rickettsii* antibodies or specific binding fragments thereof. The assays reagents are substances, mixtures, materials, or components that are useful to carry out an intended purpose of the kit. Reagents can include, for example, a conjugation reagent, a buffer, standard, positive control, label, a sample collection device, instructions and the like.

A kit can include one or more buffers, such as a wash buffer. A wash buffer can include, for example, tris(hydroxymethyl)aminomethane (Tris)-based buffers like Tris-buffered saline (TBS) or phosphate buffers like phosphate-buffered saline (PBS). Wash buffers can be composed of, for example, detergents, such as ionic or non-ionic detergents. In some embodiments, a wash buffer can be a PBS buffer at about pH 7.0, 7.2, 7.4, 7.6, 7.8 including Tween™20 (polysorbate) at about 0.001, 0.01, 0.02, 0.03, 0.04, 0.05, 0.06, 0.07, 0.08% or more.

A kit can include a dilution buffer. Dilution buffers include, for example, a carrier protein such as bovine serum albumin (BSA) and a detergent such as Tween®20 (polysorbate).

A kit can include a detection or assay buffer. A detection or assay buffer can be, for example, a colorimetric detection or assay buffer, a fluorescent detection or assay buffer, or a chemiluminescent detection or assay buffer. Colorimetric detection or assay buffers include, for example, PNPP (p-nitrophenyl phosphate), ABTS (2,2'-azino-bis(3-ethyl-benzothiazoline-6-sulphonic acid)) or OPD (o-phenylenediamine). Fluorescent detection or assay buffers include QuantaBlu® or QuantaRed® (Thermo Scientific, Waltham, MA). Chemiluminescent detection or assay buffers can include luminol or luciferin. Detection or assay buffers can also include a trigger such as $H_2O_2$ and a tracer such as isoluminol-conjugate.

A kit can include a stop solution. Stop solutions of can terminate or delay the further development of the detection reagent and corresponding assay signals. Stop solutions can include, e.g., low-pH buffers (e.g., glycine-buffer, pH 2.0), chaotrophic agents (e.g., guanidinium chloride, sodium-dodecylsulfate (SDS)), reducing agents (e.g., dithiothreitol, β-mercaptoethanol), or the like.

A kit provided can include a device for collecting a biological sample, such as collection tubes, columns, swabs, syringes, and needles. A kit can include instructions for using the components of the kit. The instructions can provide details regarding protocols and analytical techniques.

Components of a kit can be in any physical state. For example, one or more of the components can be lyophilized, in aqueous solution, or frozen.

A kit of can be designed for specific assay technologies. For example, a kit can be an immunoassay kit, a competitive immunoassay kit, a sandwich immunoassay kit, an enzyme-linked immunosorbent assay (ELISA) kit, an immunohistochemical assay kit, a turbidimetric immunoassay kit, a particle-enhanced turbidimetric immunoassay kit, a radio-immunoassay (RIA) kit, a fluorescent immunosorbent assay (FIA) kit, a multiplex immunoassay kit, a protein/peptide array immunoassay kit, a solid phase radioimmunoassay (SPRIA) kit, an indirect immunofluorescence assay (IIF) kit, a chemiluminescent immunoassay (CIA) kit, a particle based multianalyte test (PMAT) kit, a dot blot assay kit, or a western blot assay kit, a surface plasmon resonance (SPR) kit, an isothermal titration calorimetry (ITC) kit, a microscale thermophoresis (MST) kit, a biolayer interferometry kit, or grating-coupled interferometry kit. In an embodiment, an ELISA kit can include, for example, a wash buffer, sample diluent, a secondary antibody, a secondary antibody-enzyme conjugate, a detector polypeptide, a labeled detector polypeptide, a detection reagent, and a stop solution. In an embodiment a dot blot kits can include, for example, a wash buffer, sample diluent, a secondary antibody-enzyme conjugate, a detection reagent, and a stop solution. In some embodiments, a chemiluminescent immunoassay kit can include a wash buffer, a sample diluent, a tracer (e.g., isoluminol-conjugate) and a trigger (e.g., $H_2O_2$). In an embodiment, a multiplex kit can include, for example, a wash buffer, a sample diluent, and a secondary antibody-enzyme conjugate.

Methods of Treatment

Once detected or diagnosed, RMSF can be treated with, for example, antibiotic drugs, protein or peptide drugs, nucleic acid-based drugs, anti-inflammatory drugs, other drugs, immunomodulatory treatments, alternative therapies, or combinations thereof.

For example, RMSF can be treated with a number of antibiotics, for example, doxycycline (Monodox, Vibramycin), tetracycline (oxytetracycline), azithromycin, chloramphenicol (Chloromycetin), trovafloxacin (Trovan), minocycline derivatives (see e.g., US20160030452), and beta-lactamase inhibitors (see e.g., US20130023512). Doxycycline can be administered to adults at about 50, 100, 150, 200 mg every 6 hours, every 12 hours, once a day, or once every other day for 2, 4, 6, 8, 10, 12, 14 days or more. Children under 45 kg can be administered about 1.0, 2.0, 2.2, 3.0, 4.0 mg/kg body weight or more every 6 hours, every 12 hours, once a day, or once every other day for 2, 4, 6, 8, 10, 12, 14 days or more.

Protein or peptide drugs suitable for RMSF treatment include, for example, isolated chimeric outer surface protein A (OspA) (see e.g., US20180296656, US20160333056), γ-AApeptides (see e.g., US20150274782), monoclonal antibodies specific for flagellin (see e.g., US20100239583), peptide compounds for treating non-inflammatory musculoskeletal pain or osteoarthritic pain (see e.g., US 20080280835), and heterologous recombinant Sca5/OmpB protein-based vaccines.

RMSF can be treated with nucleic acid based drugs, derivatives thereof (see e.g., US2012002104, US20090324584), and lipid-modified nucleic acids (see e.g., US20070280929).

RMSF can be treated with anti-inflammatory drugs, for example, cellulose sulfate polymers or chitosan (negatively charged) polymers (see e.g., US20090298792), platelet activating factor (PAF) inhibitors and antioxidants that interferes with the arachidonic acid cascade (see e.g., US 20040022879), and prednisolone or other steroids at anti-inflammatory or immunosuppressive dosages.

RMSF can be treated with, for example, immunomodulatory compounds (see e.g., US20110184025), such as enantiomerically pure 4-(amino)-2-(2,6-dioxo(3-piperidyl))-isoindoline-1,3-dione or 3-(4-amino-1-oxo-1,3-dihydro-isoindol-2-yl)-piperidine-2,6-dione) administered alone or with an antibiotic, functional immunostimulatory protein CD40L, constitutively active TLR4 (caTLR4), functional immunostimulatory protein CD70 (see e.g., US20170000881), and/or intravenous immunoglobulin therapy.

RMSF can also be treated with a number of additional drugs that encompass pharmaceutical and/or dietary supplements of copper (I) complex with glycine, pyruvate, and/or succinic acid (see e.g., US20180071336), isothiocyanate functional surfactants (see e.g., US 2018/0311202), isooxazoline compositions used as antiparasitics such as 4-(isoxazolinyl)-benzamides (e.g., substituted 4-(5-(halomethyl)-5-phenyl-isoxazolin-3-yl)-benzam ides) and 4-(isoxazolinyl)-benzothioamides (e.g., substituted 4-(5-(halomethyl)-5-phenyl-isoxazolin-3-yl)-benzothioamides) (see e.g., US20180155301), pyrazolo[1,5-a][1,3,5]triazine derivatives and pharmaceutically acceptable salts thereof (see e.g., US20150111873), topically administering an electrolytic acid water comprising free chlorine (see e.g., US20130259955), proteasome inhibitors (see e.g., US20110172285), polymorphs of the hydrochloride salt (S)-3-aminomethyl-7-(3-hydroxy-propoxy)-3H-benzo[c][1,2]oxaborol-1-ol (see e.g., US20110152217), pyridinylamines (see e.g., US20090196912), heterobicyclic compounds (such as 4,5,6,7-tetrahydrobenzo[b]thiophene-3-carboxylic acid amides, 4,7-dihydro-5H-thieno[2,3-c]thiopyran 3-carboxylic acid amides, 4,7-dihydro-5H-thieno[2,3-c]pyran-3-carboxylic acid amides, or benzo[b]thiophene-3-carboxylic acid amides) and pharmaceutically acceptable salts (see e.g., US20070275962), pyrazine derivatives (see e.g., US20080194574), aromatic amidine inhibitors of trypsin-like proteases (such as bis(5-amidino-2-benzimidazolyl)-methane, 1,2-bis(5-amidino2-benzimidazolyl)ethane, 1,5-bis(5-amidino-2-benzimidazolyl)pentane, and 5-amidinoindole), and/or ATP synthase inhibitor for treating diseases and conditions associated with mitochondrial function (see e.g., US20090275099).

RMSF can also be treated with antimicrobial compounds as described in US20140256826 or compositions of high penetration compositions (HPC) or high penetration prodrugs (HPP) of antimicrobials and antimicrobial-related compounds (see e.g., US20130018029).

RMSF can also be treated with, for example, sonic lysates of recombinant *E. coli*, anti-TNF-alpha inhibitor, and/or nuclear factor kappa B.

Alternative therapies for treatment of RMSF include increased fluid intake, decreased glucose and sugar intake, decreased high-fat foods that slow digestion, small meals, mild or bland food diet, probiotic products such a kombucha or miso soup, magnesium, potassium, calcium, *chlorella, spirulina*, essential oil mixtures (peppermint oil, cypress oil, and coconut oil, for example), ginger, chamomile tea, vitamin B6, lemon, a phenolic-rich maple syrup extract administered with at least one antibiotic (see e.g., US 20160339071), a cool compress to the forehead or back of neck, acupuncture, and/or sitting upright after eating.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Example 1: SCA2 Polypeptides

An autochaperone domain (AC) of the extracellular protein SCA2, was discovered that comprises a stretch of amino acids that is only present in *R. rickettsii* strains. The entire unique region (boxed in FIG. 3) was named PDX6. A slightly truncated boxed region (FIG. 3) was named PDX7.

Two recombinant fusion proteins were made by fusion of 3 PDX6 repeats ("TDX1779) or 5 PDX6 repeats ("TDX1780"). See FIG. 3. In this example TDX1779 and TDX1780 additionally comprise an epitope tag at the carboxy termini of the polypeptides and a secretory (signal) sequence at the n termini of the polypeptides. PDX7, TDX1779 and TDX1780 were coated to barcoded magnetic beads (BMBs). PDX7 was linked onto an amino activated bead with an SM(PEG)12 linker (ThermoFisher). TDX1779 and TDX1780 were linked onto carboxy activated beads with an EDAC linker. The PDX, TDX1779, and TDX1780 linked beads were tested for reactivity on both indirect and direct formats.

Figure 4:
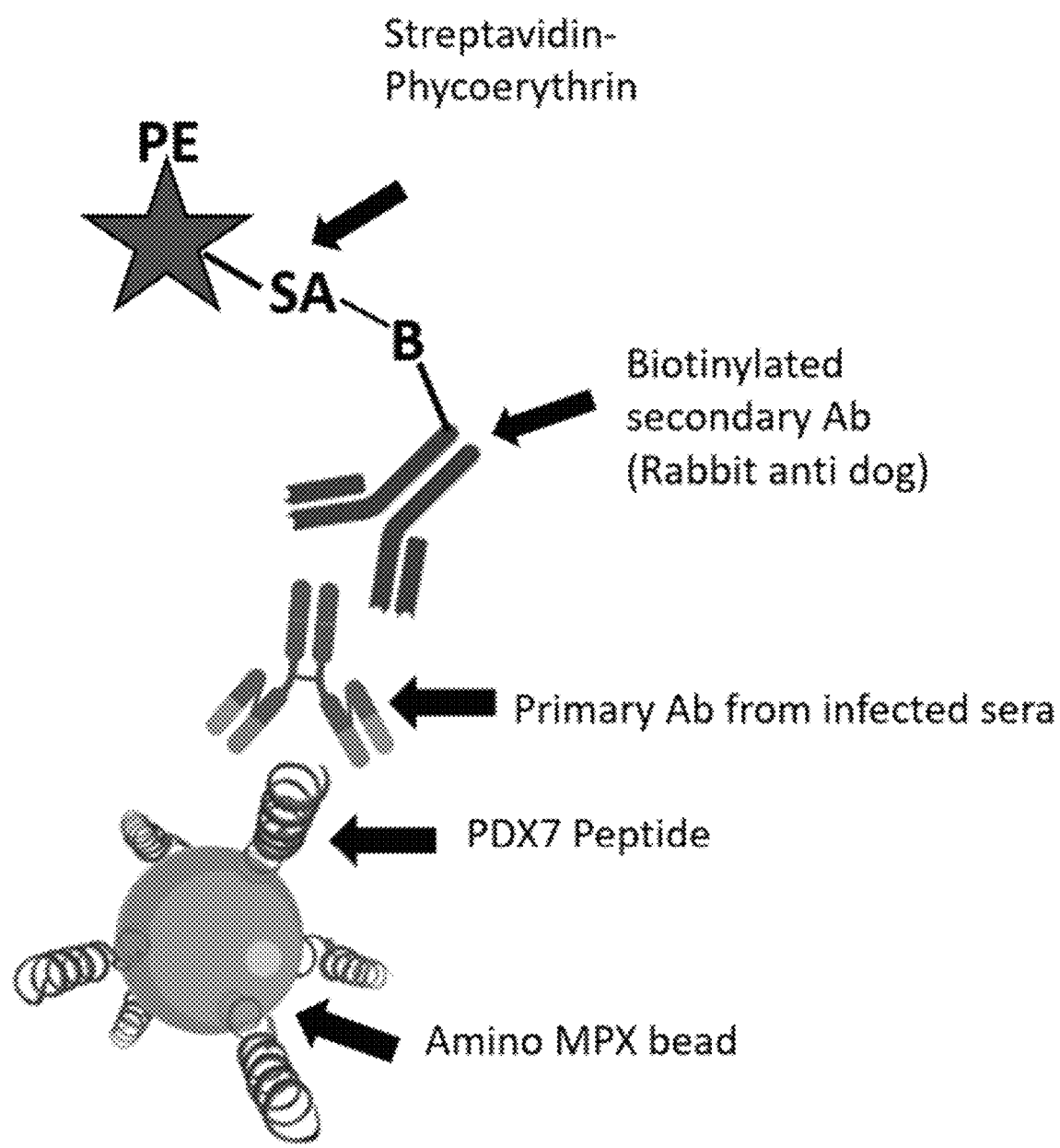

PDX7, TDX1779 and TDX1780 were tested for reactivity in multiplex using an indirect (anti-species antibody) format. A diagram of the indirect methodology is shown in FIG. 4. Briefly, a primary antibody that specifically binds one or more epitopes present in PDX7, TDX1779, or TDX1780

(from, for example, an infected dog) can specifically bind to a PDX7, TDX1779 and TDX1780 peptide coated bead. A labeled (e.g., biotinylated) secondary antibody (e.g., an anti-species antibody, in this case a rabbit anti-dog antibody) specifically binds to the primary antibody. Streptavidin-phycoerythrin can be used to detect the bead-peptide-primary antibody-labeled secondary antibody complex.

Figure 5:
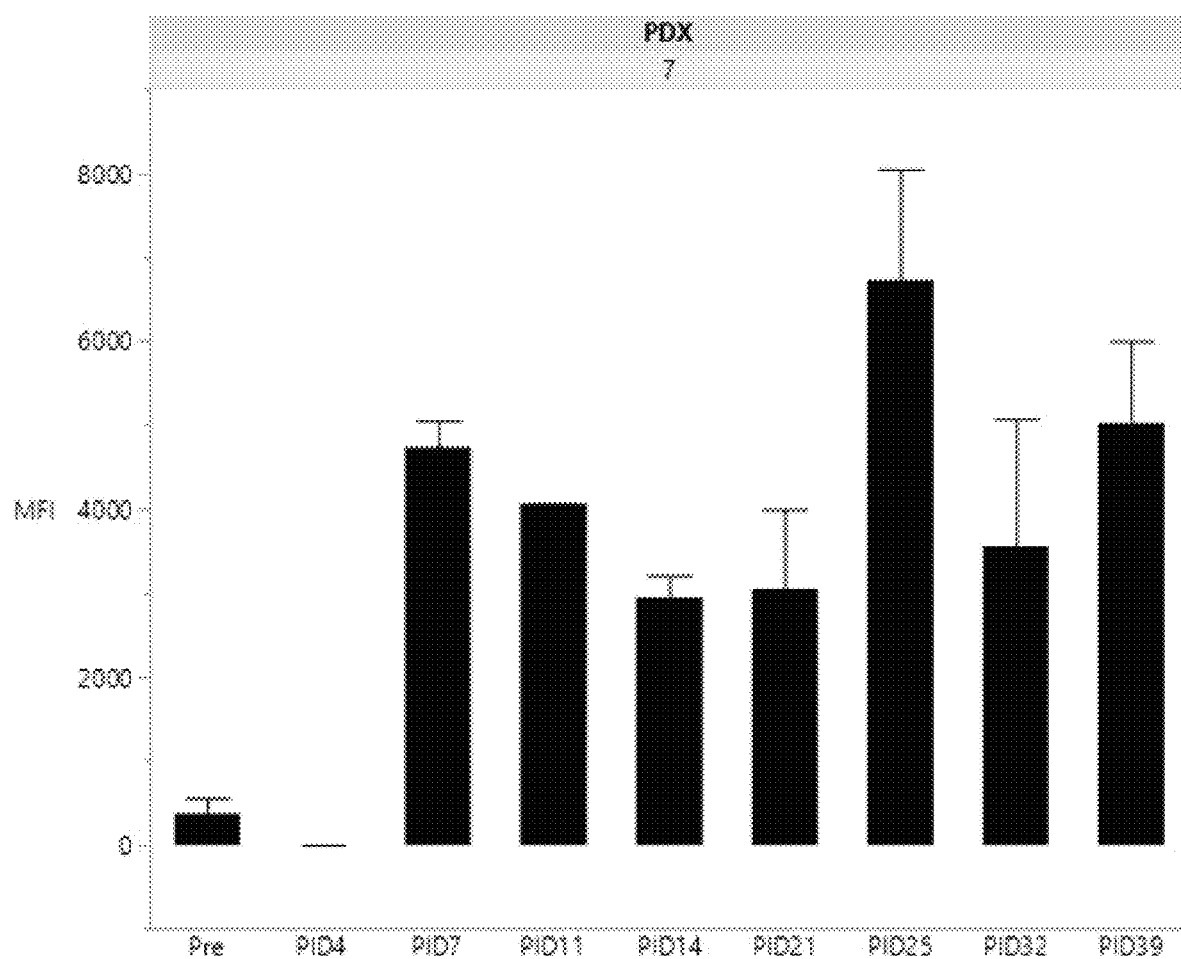

PDX7 was conjugated to amino activated beads and incubated with pooled serum from *R. rickettsia* experimentally infected canines. Detection of the antibody binding was reported using biotinylated rabbit anti-canine IgG. The results are shown in FIG. 5 (PID means post-infection day). PDX7 was able to detect infection by the seventh day post infection.

Figure 6:
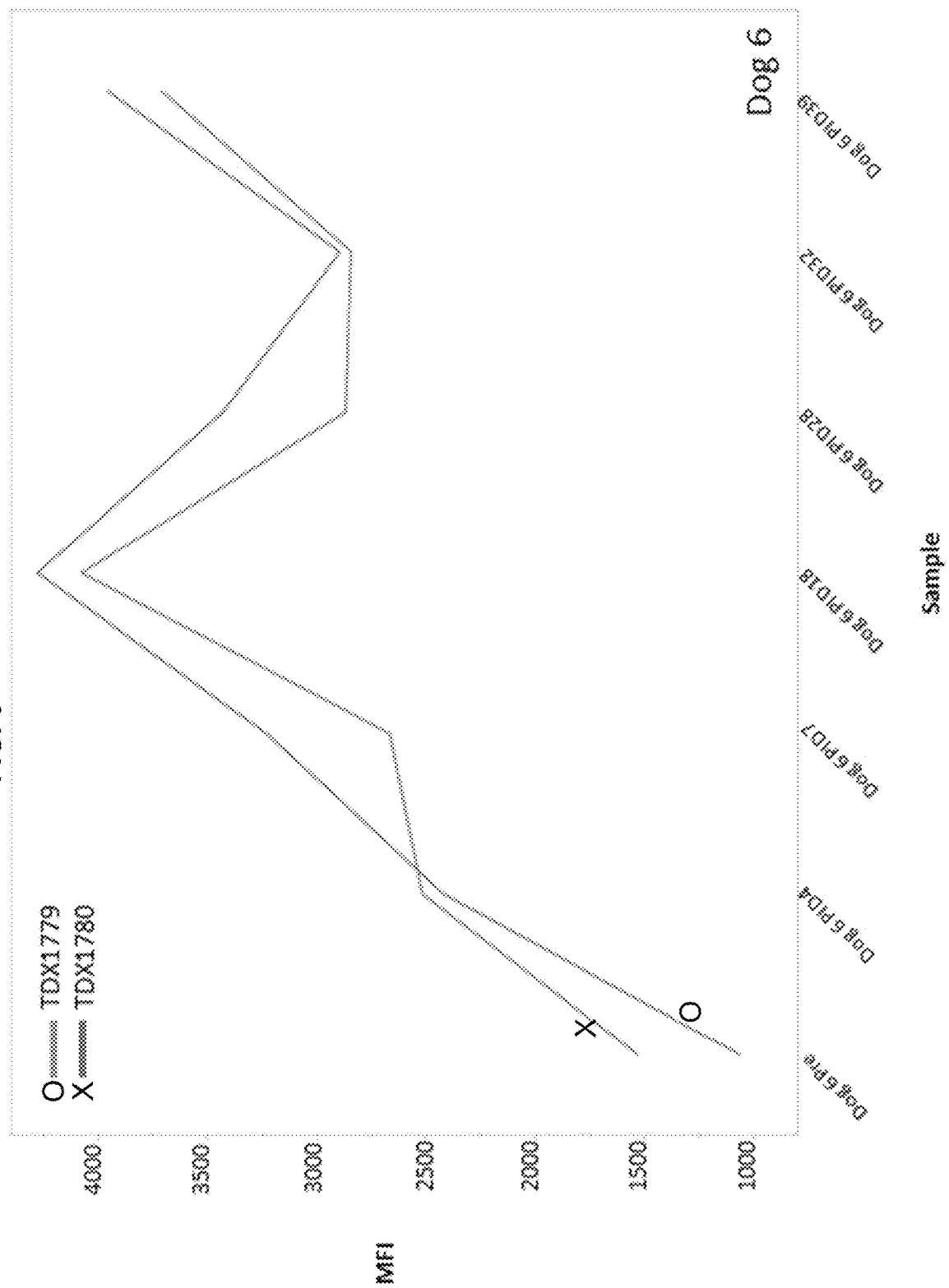
Figure 6:
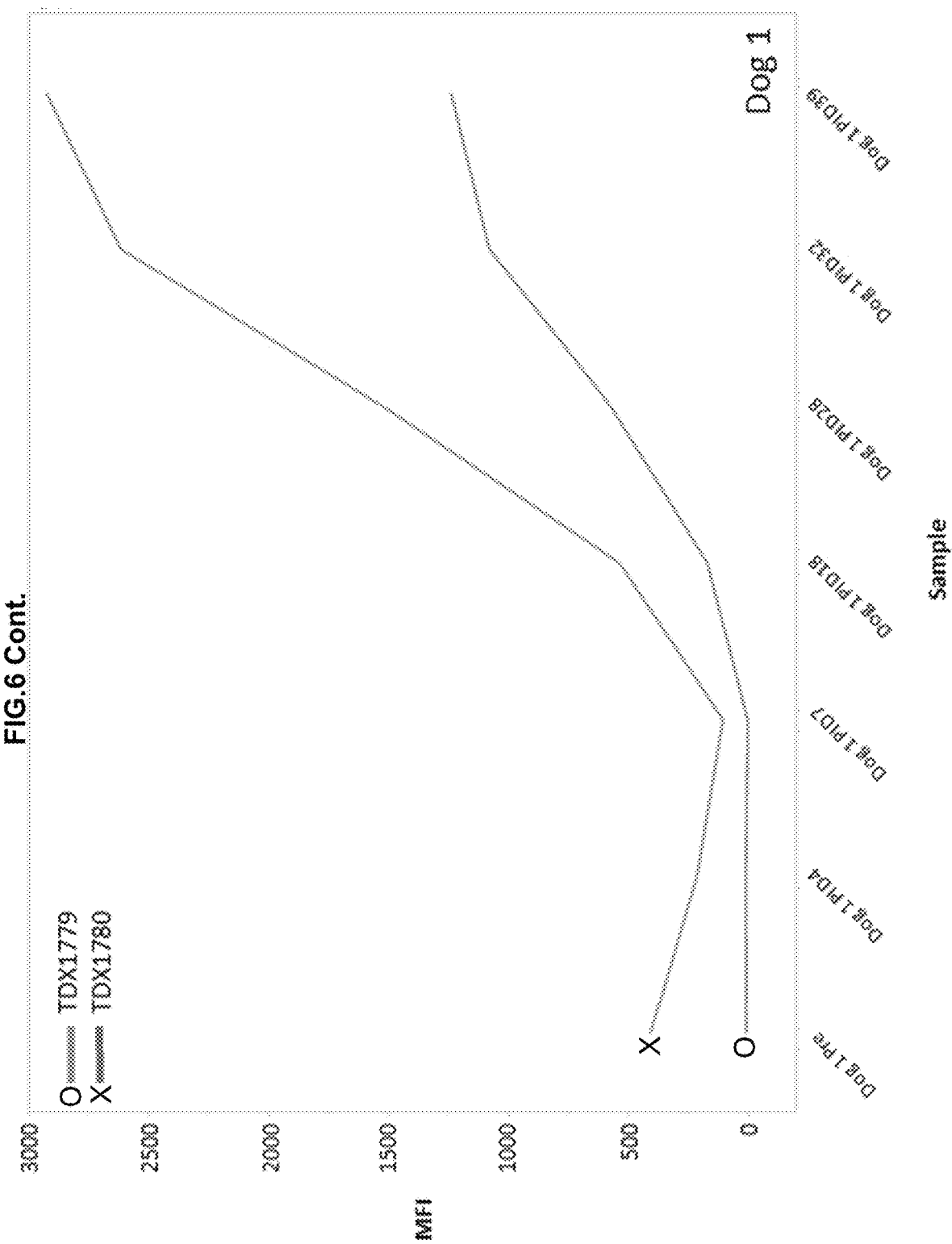

TDX1779 and TDX1780 were coupled to carboxy beads and incubated against serum from *R. rickettsii* experimentally infected canines. Detection of the antibody binding was reported using biotinylated rabbit anti canine IgG. FIG. 6 shows TDX1779 and 1780 reactivity to experimental sera in the indirect anti-species format. TDX1779 and TDX1780 were able to detect antibodies in about 7 days after infection to varying extents depending on the dog tested.

Figure 7:
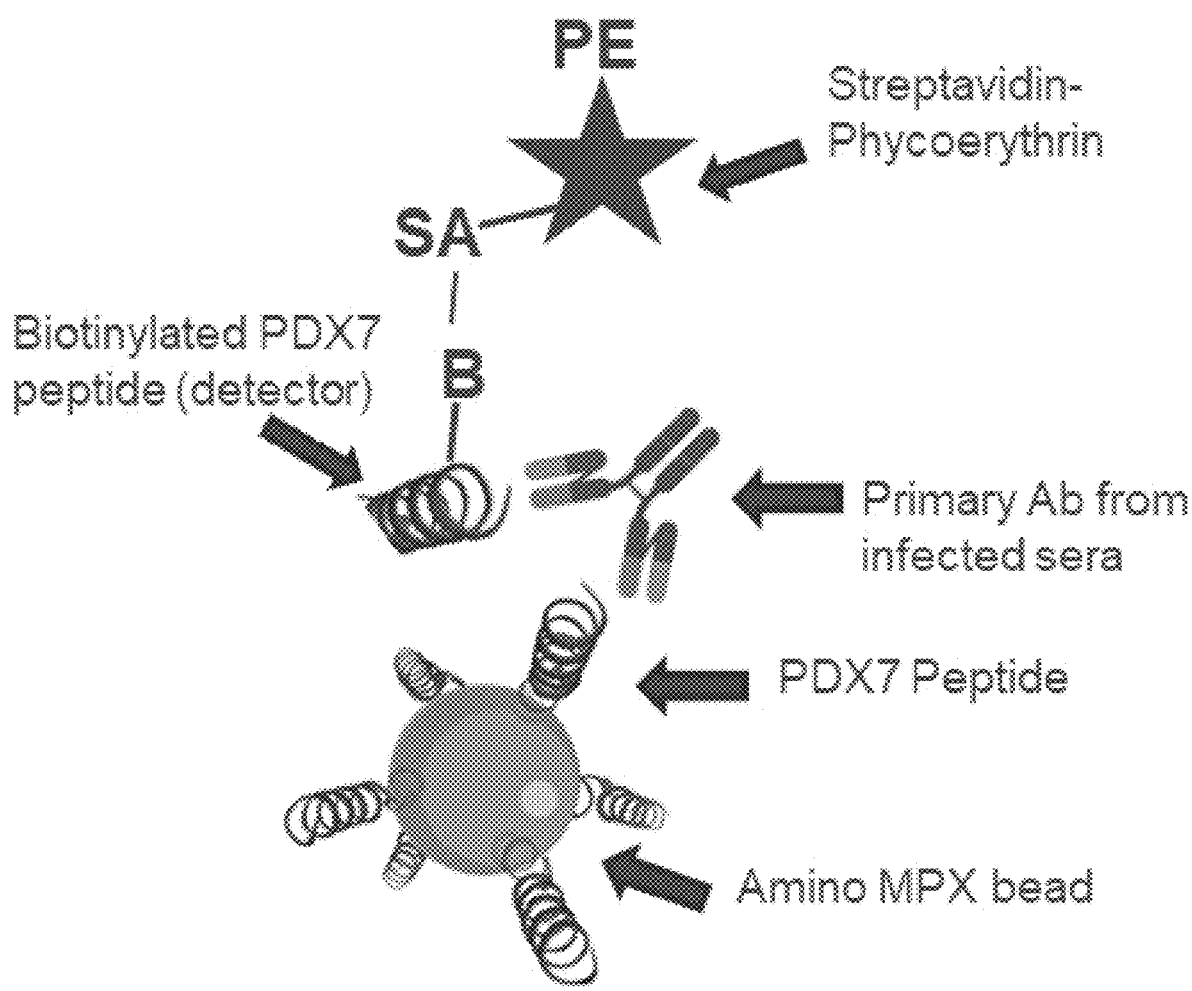

PDX7, TDX1779 and TDX1780 were also tested for reactivity in a direct (e.g., biotinylated analyte) format. A diagram of the direct methodology is shown in FIG. 7. Briefly, a primary antibody that specifically binds one or more epitopes present in PDX7, TDX1779, or TDX1780 (from, for example, an infected dog) can specifically bind to a PDX7, TDX1779 and TDX1780 peptide coated bead. A detector polypeptide (e.g., a PDX7, TDX1779 and TDX1780 polypeptide) can also specifically bind to the primary antibody. The detector polypeptide can be labeled with, for example, biotin. Streptavidin-phycoerythrin can be used to detect the bead-peptide-primary antibody-detector complex.

Figure 8:
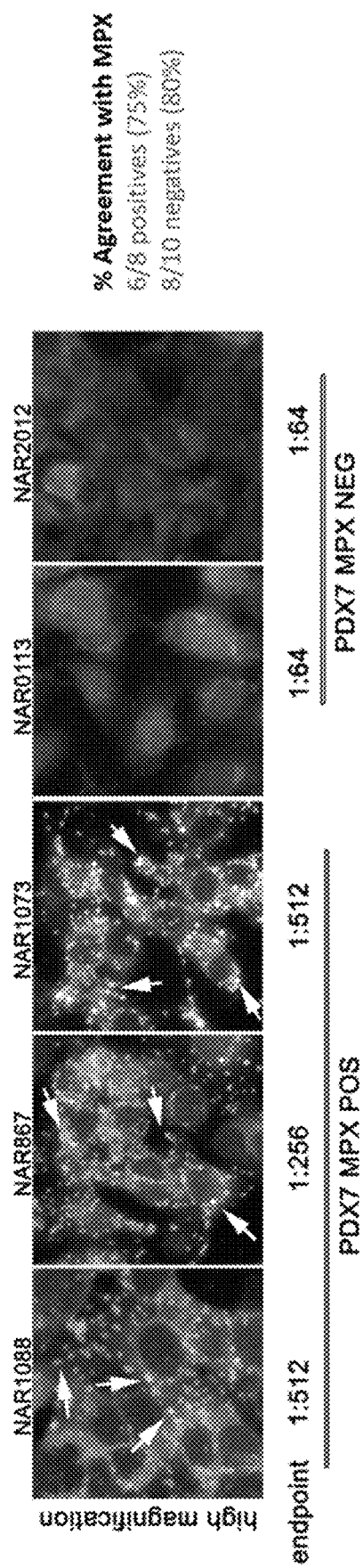

PDX7 peptides were conjugated to amino beads and screened against 574 samples from the United States using the direct assay format in which biotinylated peptide is used as a detector polypeptide. Using this approach, 8 positive samples were identified out of 574 tested (1.4% positivity; 98.6% negativity). The 8 positives were further evaluated on an IDEXX RMSF IFA for confirmation of positivity. 6 of the 8 PDX7 positive samples by multiplex were confirmed positive by IFA, suggesting strong sensitivity of PDX7 peptide for capturing anti-*Rickettsia rickettsii* antibodies. See FIG. 8 showing 75% agreement with IFA for positive samples (6/8 positives) and 80% agreement with negative samples (8/10 positives).

PDX7, TDX1779 and TDX1780 coated beads were incubated against RMSF negative (neg) or positive (pos) serum from the IDEXX Reference lab in Sacramento and detected using biotinylated TDX1779 as the conjugate. This data suggests that presumed negative serum is negative with these markers and presumed positive serum reacts. It is worth noting that all presumed positives are not expected to react because the marker is predicted to have much higher specificity for *R. rickettsii* infection whereas IFA cannot distinguish between *Rickettsia* species. See Table 1.

TABLE 1

| Analyte | RMSF IFA Neg. reactivity | RMSF IFA Pos. reactivity | RMSF IFA negative agreement | RMSF IFA positive agreement |
| --- | --- | --- | --- | --- |
| PDX7 | 0/59 | 2/36 | 100% | 5.6% |
| TDX1779 | 2/59 | 6/36 | 96.6% | 16.7% |
| TDX1780 | 2/59 | 4/36 | 96/6% | 11.1% |

PDX6, PDX7, TDX1779 and TDX1780 (SEQ ID NOs: 1-4, respectively) were tested for their ability to specifically bind antibodies against *R. rickettsii*. Beads coated with PDX6, PDX7, TDX1779 or TDX1780 (SEQ ID NOs:1-4, respectively) were incubated with each of 275 canine sera and detected using biotinylated TDX1779 (SEQ ID NO:3) as the conjugate in the direct format, using streptavidin-phycoerythrin as the label. The 275 sera were selected based on their test results for other tickborne pathogens (43 sera had each tested positive for antibodies against one of several tickborne pathogens as follows: 18 sera had tested positive for antibodies against *Anaplasma* ssp.; 11 sera had tested positive for antibodies against *Ehrlichia canis* or *Ehrlichia ewingii;* 14 sera had tested positive for antibodies against *Borrelia burgdorferi*) as well as their geographical distribution across the U.S. None of the 43 positive sera yielded a positive result with TDX1779 and TDX1780 (100% specificity) (SEQ ID NOs:3-4, respectively). One of the 43 positive sera (i.e., one of the sera positive for antibodies against *Anaplasma* ssp.) yielded a positive result with PDX6 and PDX7 (at least 97.7% specificity) (SEQ ID NOs:1-2, respectively). This data demonstrates that PDX6, PDX7, TDX1779 and TDX1780 (SEQ ID NOs:1-4, respectively) each bind patient antibodies against *R. rickettsii* with high specificity. This data also demonstrates that a highly specific assay for antibodies against *R. rickettsii* can be built with PDX6, PDX7, TDX1779 and TDX1780 (SEQ ID NOs:1-4, respectively).

Example 2

Figure 9:
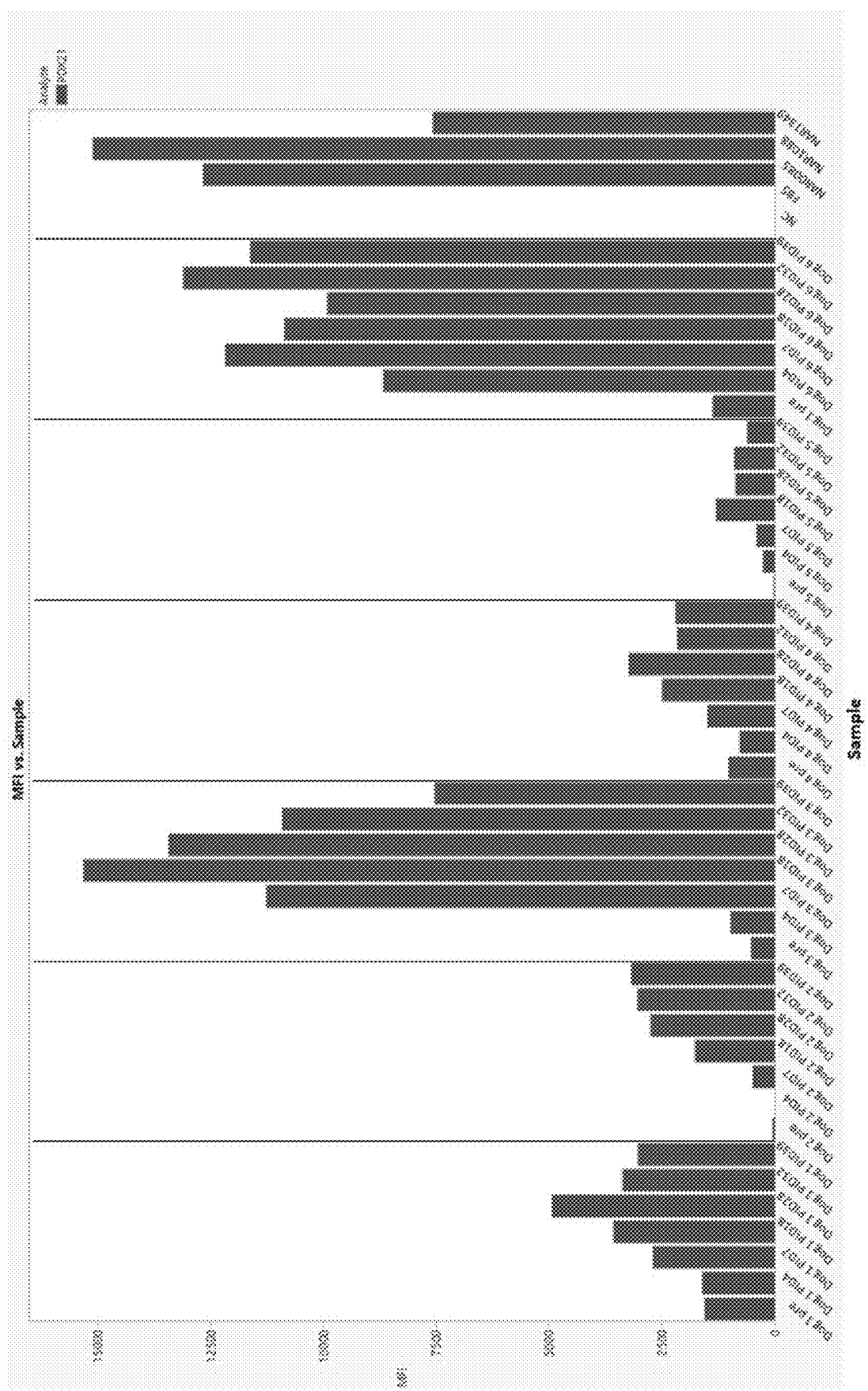

Serum from *R. rickettsii* experimentally infected canines was evaluated for reactivity to PDX21 polypeptide (SEQ ID NO:5) on the ABC multiplex platform using biotinylated rabbit anti-canine as the detector. In FIG. 9 individual dogs 1-6 (left to right) are separated by vertical black lines. For each experimentally infected canine, pre immune sera "Pre" was compared to sera from post-infection day 4, 7, 18, 28, 32 and 39 as indicated by the numbers after the dogs. While each dog exhibited varying baseline reactivity, all six dogs showed increased reactivity to PDX21 from between days 7-18 post infection compared to respective pre-immune sera. Reactivity to PDX21 peaked by day 28-32 post infection and either plateaued or began declining thereafter. To the far right of FIG. 9 negative and positive controls are shown. NC=BSA/PBS as the sample, FBS=fetal bovine serum as the sample, positive controls (PC) are NAR0085, 1088 and 1349 are confirmed RMSF positive samples and showed strong reactivity to PDX21, highlighting the reactivity of VUT protein-derived PDX21 peptide to serum from *R. rickettsii* naturally and experimentally infected canine serum.

We claim:

1. A polypeptide comprising:
   (i) 90% or more sequence identity to the polypeptide as set forth in SEQ ID NO: 3, 4, 5, 6, or 7;
   (ii) a fusion protein comprising two, three, four, five, six, seven or more polypeptides having 90% or more sequence identity to SEQ ID NO:1, 2, 3, 4, 5, 6, or 7; or
   (iii) a fusion protein comprising at least two polypeptides having 90% or more sequence identity to SEQ ID NO: 3, 4, 5, 6, or 7;
   (iv) the polypeptide as set forth in SEQ ID NO:1 or 2.

2. The polypeptide of claim 1, wherein the polypeptide has less than 75 total amino acids.

3. The polypeptide of claim 1, wherein the polypeptide is as set forth in SEQ ID NO:3 or 4 and has less than 350 total amino acids.

4. The polypeptide of claim 1, wherein the polypeptide is lyophilized, desiccated, or dried.

5. The polypeptide of claim 1, wherein the polypeptide further comprises one or more labels or tags.

6. The polypeptide of claim 1, wherein the polypeptide is immobilized to a support.

7. The polypeptide of claim 1, wherein the polypeptide is present in an immunocomplex with one or more antibodies that specifically bind to a polypeptide as set forth in SEQ ID NO:1, 2, 3, 4, 5, 6, or 7.

8. The polypeptide of claim 1, wherein the polypeptide comprises 90% or more sequence identity to the polypeptide as set forth in SEQ ID NO: 5, 6, or 7 and one or more secretory signal sequences, one or more epitope tags, or one or more secretory signal sequences and one or more epitope tags or wherein the polypeptide comprises the sequence as set forth in SEQ ID NO:1 or 2 and one or more secretory signal sequences, one or more epitope tags, or one or more secretory signal sequences and one or more epitope tags.

9. A method of detecting anti-*Rickettsia rickettsia* antibodies or specific binding fragments thereof comprising (a) contacting a test sample with one or more polypeptides as set forth in SEQ ID NO:1, 2, 3, 4, 5, 6, or 7; and (b) detecting complexes of anti-*Rickettsia rickettsii* antibodies or specific binding fragments thereof and the one or more polypeptides.

10. The method of claim 9, wherein the one or more polypeptides are immobilized to a support.

11. The method of claim 9, wherein the complexes are detected using one or more secondary antibodies or specific binding fragments thereof that specifically bind anti-*Rickettsia rickettsii* antibodies or specific binding fragments thereof.

12. The method of claim 11, wherein the secondary antibodies or specific binding fragments thereof comprise one or more tags or labels.

13. The method of claim 9, wherein the complexes are detected using one or more detector polypeptides comprising 90% or more sequence identity to a polypeptide as set forth in SEQ ID NO:1, 2, 3, 4, 5, 6, or 7.

14. The method of claim 13, wherein the one or more detector polypeptides comprise a label or tag.

15. A method for diagnosing a disease caused by *Rickettsia rickettsii* in a subject by (a) contacting a test sample with one or more polypeptides as set forth in SEQ ID NO:1, 2, 3, 4, 5, 6, or 7; and (b) detecting complexes of anti-*Rickettsia rickettsii* antibodies or specific binding fragments thereof and the one or more polypeptides.

16. The method of claim 15, wherein the subject has been infected with *Rickettsia* for less than 7 days.

17. The method of claim 15, further comprising comparing an amount of the complexes in the sample to a control sample or control standard, wherein elevated levels of the complexes as compared to the control sample or control standard is an indication of a disease caused by *Rickettsia rickettsii*.

18. The method of claim 15, further comprising administering a treatment for a disease caused by *Rickettsia rickettsii* where the complexes are detected.

19. The method of claim 15, further comprising determining an amount of the anti-*Rickettsia rickettsii* antibodies or specific binding fragments thereof in the sample.

20. The method of claim 15, wherein the subject is a non-human animal.

21. The method of claim 15, wherein the test sample is blood, plasma, serum, or lymph fluid.

22. A kit for diagnosing a disease caused by *Rickettsia rickettsii*, the kit comprising:
    (a) one or more polypeptides of claim 1, wherein the one or more polypeptides are not naturally occurring; and
    (b) one or more reagents that facilitate binding of the one or more polypeptides to anti-*Rickettsia rickettsii* antibodies or specific binding fragments thereof present in a test sample.

23. A composition comprising:
    a polypeptide having 90% or more sequence identity to amino acids 21-161 (PDX6x3) of SEQ ID NO:3 and further comprising an epitope tag, a secretory signal, or both an epitope tag and a secretory signal.

\* \* \* \* \*